(12) United States Patent
Muchowski et al.

(10) Patent No.: US 7,618,793 B2
(45) Date of Patent: Nov. 17, 2009

(54) IDENTIFYING AGENTS FOR DECREASING CELLULAR TOXICITY ASSOCIATED WITH HUNTINGIN POLYPEPTIDE

(75) Inventors: Paul J. Muchowski, Sunnyvale, CA (US); Flaviano Giorgini, Leicester (GB)

(73) Assignee: The Regents of the University of Washington, Seattle, WA (US)

( * ) Notice: Subject to any disclaimer, the term of this patent is extended or adjusted under 35 U.S.C. 154(b) by 0 days.

(21) Appl. No.: 10/970,741

(22) Filed: Oct. 20, 2004

(65) Prior Publication Data

US 2006/0084072 A1   Apr. 20, 2006

(51) Int. Cl.
*G01N 33/53* (2006.01)
*C12P 21/06* (2006.01)
*C12N 15/74* (2006.01)
*A01N 63/04* (2006.01)
*A61K 49/00* (2006.01)

(52) U.S. Cl. .................. 435/7.31; 435/69.9; 435/483; 424/93.51; 424/9.1

(58) Field of Classification Search ........................ None
See application file for complete search history.

(56) References Cited

U.S. PATENT DOCUMENTS

2003/0073610 A1    4/2003    Lindquist et al.

OTHER PUBLICATIONS

Li et al. Trends in Genetics 2004. 20:146-154.*
/www.yeastgenome.org/sgdpub/Saccharomyces_cerevisiae.pdf.*
Ambrose, C. et al., "Structure and expression of the Huntington's disease gene: evidence against simple inactivation due to an expanded CAG repeat," *Somat. Cell. Mol. Genet.*, 20(1):27-38 (Jan. 1994).
Cowles, C. et al., "Mutations in the *VPS45* gene, a *SEC1* homologue, result in vacuolar protein sorting defects and accumulation of membrane vesicles," *J. Cell Sci.*, 107:3449-3459 (1994).
Dailey, D. et al., "Novel yeast protein kinase (*YPK1* gene product) is a 40-kilodalton phosphotyrosyl protein associated with protein-tyrosine kinase activity," *Mol. Cell. Biol.*, 10(12):6244-6256 (Dec. 1990).
Gusella, J. and Macdonald M., "Molecular genetics: Unmasking polyglutamine triggers in neurodegenerative disease," *Nat. Rev. Neurosci.*, 1(2):109-115 (Nov. 2000).
Hardy J. and Selkoe D., "The amyloid hypothesis of Alzheimer's disease: Progress and problems on the road to therapeutics," *Science*, 297(5580):353-356 (Jul. 19, 2002).
Macdonald, M. et al., "A novel gene containing a trinucleotide repeat that is expanded and unstable on Huntington's disease chromosomes," The Huntington's Disease Collaborative Research Group, *Cell*, 72(6):971-983 (Mar. 26, 1993).
Meriin, A. et al., "Huntington toxicity in yeast model depends on polyglutamine aggregation mediated by a prion-like protein Rnq1," *J. Cell. Biol.*, 157(6):997-1004 (Jun. 10, 2002).

Muchowski, P. et al., "Hsp70 and Hsp40 chaperones can inhibit self-assembly of polyglutamine proteins into amyloid-like fibrils," *PNAS*, 97(14):7841-7846 (Jul. 5, 2000).
Rochet, JC and Lansbury, P., "Amyloid fibrillogenesis: themes and variations," *Curr. Opin. Struct. Biol.*, 10(1):60-68 (Feb. 2000).
Ross, C. and Poirier, M., "Protein aggregation and neurodegenerative disease," *Nat. Med.*, 10 Suppl:S10-S17 (Jul. 2004).
Scherzinger, E. et al., "Huntingtin-encoded polyglutamine expansions form amyloid-like protein aggregates in vitro and in vivo," *Cell*, 90(3):549-558 (Aug. 8, 1997).
Zoghbi, H. et al., "Glutamine repeats and neurodegeneration," *Annu. Rev. Neurosci.*, 23:217-247 (2000).
Muchowski, P. et al., U.S. Appl. No. 11/003,216, filed Dec. 3, 2004, entitled "Methods of Identifying Lead Compounds that Modulate Toxicity of Neurotoxic Polypeptides".
Burger H., et al., "A genome-wide screening in *Saccharomyces cerevisiae* for genes that confer resistance to the anticancer agent cisplatin," *Biochem. Biophys. Res. Commun.*, 269:767-774 (2000).
Chiarugi A., et al., "Kynurenine 3-mono-oxygenase activity and neurotoxic kynurenine metabolites increase in the spinal cord of rats with experimental allergic encephalomyelitis," *Neuroscience*, 102(3):687-695 (2001), Abstract.
Cozzi A., et al., "Kynurenine hydroxylase inhibitors reduce ischemic brain damage: studies with (m-nitrobenzoyl)-alanine (mNBA) and 3,4-dimethoxy-[-N-4-(nitrophenyl)thiazol-2yl]-benzenesulfonamide (Ro 61-8048) in models of focal or global brain ischemia," *J. Cereb. Blood Flow Metab.*, 19(7):771-777 (1999), Abstract.
Meriin A., et al., "Aggregation of expanded polyglutamine domain in yeast leads to defects in endocytosis," *Mol. Cell. Biol.*, 23(21):7554-7565 (Nov. 2003).
Meriin A., et al., "Huntington toxicity in yeast model depends on polyglutamine aggregation mediated by a prion-like protein Rnq1," *J. Cell Biol.*, 157(6):997-1004 (Jun. 10, 2002).
Moroni F. et al. "Studies on the neuroprotective action of kynurenine mono-oxygenase inhibitors in post-ischemic brain damage," *Adv. Exp. Med. Biol.*, 527:127-136 (2003).
Moroni, et al., "Neuroprotective effects of kynurenine-3-hydroxylase inhibitors in models of brain ischemia," *Adv. Exp. Med. Biol.*, 467:199-206 (1999), Abstract.
Munder T. and Hinnen A., "Yeast cells as tools for target-oriented screening," *Appl. Microbol. Biotechnol.*, 52:311-320 (1999).
Obrenovitch TP and Urenjak J., "In vivo assessment of kynurenate neuroprotective potency and quinolinate excitotoxicity," *Amino Acids*, 19(1):299-309 (2000), Abstract.

(Continued)

*Primary Examiner*—Christine J Saoud
*Assistant Examiner*—Chang-Yu Wang
(74) *Attorney, Agent, or Firm*—Townsend and Townsend and Crew LLP

(57) ABSTRACT

Methods of screening candidate agents to identify potential therapeutic agents for the treatment of a neurodegenerative disease, such as Huntington's Disease and Parkinson's Disease and methods for identifying a mutation in, or changes in expression of, a gene associated with neurodegenerative disease, such as Huntington's Disease and Parkinson's Disease, are provided.

11 Claims, No Drawings

OTHER PUBLICATIONS

Perego P., et al., "Yeast mutants as a model system for identification of determinants of chemosensitivity," *Pharmacol. Rev.*, 52:477-491 (2000).

Richter A. and Hamann M., "The kynurenine 3-hydroxylase inhibitor Ro 61-8048 improves dystonia in a genetic model of paroxysmal dyskinesia," *Eur. J. Pharmacol.*, 478(1):47-52 (Sep. 2003), Abstract.

Rover S., et al., "Synthesis and biochemical evaluation of N-(4-phenylthiazol-2-yl)benzenesulfonamides as high-affinity inhibitors of kynurenine 3-hydroxylase," *J. Med. Chem.*, 40(26):4378-4385 (Dec. 1997), Abstract.

Schwarcz R., "The kynurenine pathway of tryptophan degradation as a drug target,"*Curr. Opin. Pharmacol.*, 4(1):12-7 (Feb. 2004), Abstract.

Urenjak J. and Obrenovitch TP., "Kynurenine 3-hydroxylase inhibition in rats: effects on extracellular kynurenic acid concentration and N-methyl-D-aspartate-induced depolarisation in the striatum," *J. Neurochem.*, 75(6):2427-2433 (Dec. 2000), Abstract.

Zysk J. and Baumbach W., "Homogeneous pharmacologic and cell-based screens provide diverse strategies in drug discovery: somatostatin antagonists as a case study," *Chomb. Chem. High Throughput Screen.*, 1:171-183 (1998).

* cited by examiner

IDENTIFYING AGENTS FOR DECREASING CELLULAR TOXICITY ASSOCIATED WITH HUNTINGIN POLYPEPTIDE

STATEMENT AS TO RIGHTS TO INVENTIONS MADE UNDER FEDERALLY SPONSORED RESEARCH OR DEVELOPMENT

This work was supported in part by grant number R01NS47237 from the National Institutes of Health. The U.S. Government may have certain rights in the invention.

BACKGROUND OF THE INVENTION

Huntington's disease (HD) is a fatal, inherited neurodegenerative disorder that is characterized by disturbances in movement, cognition and personality. HD is autosomal dominant. Neurodegeneration is associated with selective neuronal cell death, occurring primarily in the cortex and striatum of the brain.

The mutation that causes HD is an expansion of CAG repeats in the first exon of gene IT-15, that encodes the huntingtin protein (Huntington's Disease Collaborative Research Group, Cell 72:971-83 (1993); Ambrose et al., Somat. Cell Mol. Genet. 20:27-38 (1994)). CAG encodes the amino acid glutamine ("Gln" or "Q"), so CAG repeats encode polyglutamine (or "polyQ") regions within huntingtin. The polyglutamine region of huntingtin from non-HD individuals contains about 8-31 consecutive Gln residues. Huntingtin with over 37 consecutive Gln residues is associated with mild to severe HD, with the more severe cases exhibiting a polyglutamine region of up to about 68, or more, Gln residues. The same mutational mechanism, expansion of CAG repeats, is responsible for a growing number of less common neurodegenerative disorders that include the spinocerebellar ataxias (SCAs) (Zoghbi et al., Ann. Rev. Neurosci. 23:217-47 (2000)).

Parkinson's disease (PD) is a major neurodegenerative disorder characterized by muscle rigidity, bradykinesia, resting tremor and postural instability (Goedert, Nat. Rev. Neurosci. 2:492-501 (2001)). Although the vast majority of cases of PD are idiopathic, a small percentage of cases are caused by missense mutations in the α-synuclein gene (Polymeropoulos et al., Science 276:2045-47 (1997); Kruger et at., Nat. Genet. 18:106-08 (1998)). One neuropathological feature shared by both HD and PD is the occurrence of ubiquitinated inter-neuronal inclusion bodies in diseased brains. Huntingtin, and/or degradation products of huntingtin, are the major components of cytoplasmic and nuclear inclusion bodies that are observed in HD. α-Synuclein is the major component of inclusion bodies (called Lewy bodies) in PD.

Huntingtin and α-synuclein assemble into fibrillar protein aggregates that display many properties of amyloid in vitro and in vivo (Scherzinger et al., Cell 90:549-58 (1997); Rochet et al., Curr. Opin. Struct. Biol. 10:60-88 (2000)). The "amyloid hypothesis," developed originally to describe the role of β-amyloid in Alzheimer's Disease (AD), suggests that the aggregation of proteins into an ordered fibrillar structure is causally related to aberrant protein interactions that culminate in neuronal dysfunction and cell death (Hardy et al., Science 297:353-56 (2002)). The similar physical, biochemical, and morphological features of huntingtin, α-synuclein, and other amyloid-forming proteins have led to the speculation that neurodegeneration associated with protein misfolding may have common molecular mechanisms. However, the precise roles of protein aggregation, amyloid formation and inclusion bodies in HD, PD, and other amyloidogenic diseases remain controversial. While significant efforts have been made to understand the roles of huntingtin and α-synuclein in HD and PD, respectively, a unifying pathogenic mechanism has not been identified. Different genes and pathways have been suggested to play important roles in HD and PD (see, e.g., Goedert, Nat. Rev. Neurosci. 2:492-501 (2001); Gusella et al., Nat. Rev. Neurosci. 1:109-15 (2000)), but these suggestions remain to be confirmed. Further, the lack of tractable genetic models has impeded the identification of additional genes involved in or associated with neurotoxicity.

BRIEF SUMMARY OF THE INVENTION

The present invention provides methods for identifying a potential therapeutic agent for the treatment of amyloidogenic disease, particularly neurodegenerative amyloidogenic disease. The methods generally include (a) contacting a candidate agent with a eukaryotic cell expressing both a neurotoxic polypeptide and a wild-type gene that enhances toxicity of the neurotoxic polypeptide when expressed in the cell, and/or contacting the candidate agent with a sample of the wild-type protein encoded by the gene that enhances toxicity of the neurotoxic polypeptide, and (b) determining for the cell and/or protein sample the level of a biological activity or characteristic associated with the neurotoxic polypeptide and/or wild-type protein. Suitable eukaryotic cells for expression of the huntingtin or α-synuclein polypeptide include yeast (e.g., Saccharomyces cerevisiae), C. elegans, Drosophila, mouse, rat, and human cells. The agent can be either a synthetic compound or natural compound. Suitable candidate agents include, for example, small molecules, nucleic acids, proteinaceous agents, or peptidomimetics.

In one aspect, the method is for the identification of a potential therapeutic agent for the treatment of Huntington's Disease (HD) and includes (1) contacting a first eukaryotic cell with a candidate agent, where the first cell expresses a huntingtin polypeptide comprising an expanded polyQ repeat (e.g., an expanded polyQ repeat having at least 45 glutamine residues) and at least one of the following wild-type genes: BNA4, CYK3, ECM37, MBF1, MGT1, MSO1, PAF1, RDH54, RXT3, SNA2, KEX1, VPS53, YDR287W, YER185W, YLR278C, YMR082C, HSP104, NHP6B, SMY2, YLR454W, PHO87, BFR1, MSL1, UME-1, YMR244C-A, ARG7, YCL005W, BNA1, VPS60, YBR241C, YDR459C, YMR075C-A, YMR086W, COX5B, NUP2, YDJ1, KMO, SH3GL2, EDF1, MGMT, PD2, RAD54B, PPGB, FLJ10979, IMPA1, SKD, HMGB2, PERQ1, KIAA0100, SLC13A5, SNRPA, NUP43, HAAO, SLC2A1, ZDHHC15, SEMG2, RANBP2, and DNAJA2, and where expression of the huntingtin polypeptide is toxic to the cell; (2) contacting a second eukaryotic cell with the candidate agent, where the second cell expresses the huntingtin polypeptide and does not express the wild-type gene; and (3) determining for the first and second cells the level of a biological activity or characteristic associated with the toxicity of the huntingtin polypeptide, whereby if the first cell (a) exhibits a substantial decrease of the biological activity or characteristic relative to a control cell that has not been contacted with the candidate agent and (b) does not exhibit a substantial decrease of the biological activity or characteristic relative to the second cell, the agent is identified as a potential therapeutic agent for the treatment of HD.

In certain embodiments of the method, the wild-type gene is BNA4, CYK3, ECM37, MBF1, MGT1, MSO1, PAF1, RDH54, RXT3, SNA2, VPS53, YDR287W, YER185W, YLR278C, YMR082C, NHP6B, SMY2, YLR454W, PHO87, BFR1, UME-1, YMR244C-A, or ARG7; preferably BNA4, CYK3, MBF1, MGT1, PAF1, RDH54, VPS53, YDR287W, NHP6B, SMY2, YLR454W, PHO87, UME-1, or YMR244C-A, more preferably BNA4, CYK3, MBF1, MGT1, YDR287W, or PHO87. In other embodiments, the wild-type gene is KMO, SH3GL2, EDF1, MGMT, PD2, RAD54B, PPGB, FLJ10979, IMPA1, SKD, HMGB2, PERQ1, KIAA0100, SLC13A5, SNRPA, NUP43, HAAO, SLC2A1, ZDHHC15, SEMG2, RANBP2, or DNAJA2; preferably KMO, SH3GL2, EDF1, MGMT, PD2, RAD54B, FLJ10979, IMPA1, HMGB2, PERQ1, KIAA0100, SLC13A5, or NUP43; more preferably KMO, SH3GL2, EDF1, MGMT, IMPA1, or SLC13A5. In some variations, KMO, SH3GL2, EDF1, MGMT, PD2, RAD54B, PPGB, FLJ10979, IMPA1, SKD, HMGB2, PERQ1, KIAA0100, SLC13A5, SNRPA, NUP43, HAAO, SLC2A1, ZDHHC15, SEMG2, RANBP2, or DNAJA2 is expressed in a yeast cell that does not express the corresponding yeast ortholog of the gene, or in a human cell cultured in vitro.

Typically, the second cell, expressing the huntingtin polypeptide but not the wild-type gene, contains a null allele of the wild-type gene or has a deletion of the wild-type gene. In some variations, the biological activity or characteristic associated with the toxicity of the huntingtin polypeptide is decreased cell viability relative to a cell that does not express the polypeptide, or the formation of inclusion bodies in the cell. The contacting of the cell with the candidate agent can include, for example, transformation or culturing the cell in media containing the candidate agent. Further, in certain embodiments, the huntingtin polypeptide is a fusion protein such as, for example, a fusion protein that includes a reporter polypeptide or a myc epitope.

In a related aspect, the present invention provides methods of identifying a potential therapeutic agent for the treatment of HD that includes contacting a candidate agent with a wild-type protein encoded by a gene that enhances toxicity of a neurotoxic polypeptide. Generally, the method includes (1) contacting the wild-type protein with a candidate agent; (2) determining the level of a biological activity associated with the protein relative to a control sample of protein that has not been contacted with the candidate agent; and (3) if the first sample of protein exhibits a substantial decrease in the biological activity relative to the control sample, then (a) contacting a first eukaryotic cell expressing the protein and a huntingtin polypeptide comprising an expanded polyQ repeat (e.g., an expanded polyQ repeat having at least 45 glutamine residues), where expression of the huntingtin polypeptide is toxic to the cell; and (b) determining for the first cell the level of a biological activity or characteristic associated with the toxicity of the huntingtin polypeptide, where the level of the biological activity or characteristic is relative to a control eukaryotic cell that expresses the protein and the huntingtin polypeptide and that has not been contacted with the candidate agent, where if the first cell exhibits a substantial decrease in the biological activity or characteristic relative to the control cell, the agent is identified as a potential therapeutic agent for the treatment of HD. In some variations, the wild-type protein is expressed in a yeast cell that does not express the corresponding yeast ortholog of the gene, or in a human cell cultured in vitro. The method optionally includes contacting a second eukaryotic cell with the candidate agent, where the second cell expresses the huntingtin polypeptide comprising an expanded polyQ repeat and does not express the wild-type protein, and determining for the second cell the level of the biological activity or characteristic associated with the expression of the huntingtin polypeptide, where if the first cell exhibits a substantial decrease of the biological activity or characteristic relative to the control cell and does not exhibit a substantial decrease of the biological activity or characteristic relative to the second cell, the agent is identified as a potential therapeutic agent for the treatment of HD.

Wild-type proteins suitable for use in accordance with the above methods include BNA4, CYK3, ECM37, MBF1, MGT1, MSO1, PAF1, RDH54, RXT3, SNA2, KEX1, VPS53, YDR287W, YER185W, YLR278C, YMR082C, HSP104, NHP6B, SMY2, YLR454W, PHO87, BFR1, MSL1, UME-1, YMR244C-A, ARG7, YCL005W, BNA1, VPS60, YBR241C, YDR459C, YMR075C-A, YMR086W, COX5B, NUP2, YDJ1, KMO, SH3GL2, EDF1, MGMT, PD2, RAD54B, PPGB, FLJ10979, IMPA1, SKD, HMGB2, PERQ1, KIAA0100, SLC13A5, SNRPA, NUP43, HAAO, SLC2A1, ZDHHC15, SEMG2, RANBP2, and DNAJA2. In certain embodiments, the wild-type protein is BNA4, CYK3, ECM37, MBF1, MGT1, MSO1, PAF1, RDH54, RXT3, SNA2, VPS53, YDR287W, YER185W, YLR278C, YMR082C, NHP6B, SMY2, YLR454W, PHO87, BFR1, UME-1, YMR244C-A, or ARG7; preferably BNA4, CYK3, MBF1, MGT1, PAF1, RDH54, VPS53, YDR287W, NHP6B, SMY2, YLR454W, PHO87, UME-1, or YMR244C-A, more preferably BNA4, CYK3, MBF1, MGT1, YDR287W, or PHO87. In yet other variations, the wild-type protein is KMO, SH3GL2, EDF1, MGMT, PD2, RAD54B, PPGB, FLJ10979, IMPA1, SKD, HMGB2, PERQ1, KIAA0100, SLC13A5, SNRPA, NUP43, HAAO, SLC2A1, ZDHHC15, SEMG2, RANBP2, or DNAJA2; preferably KMO, SH3GL2, EDF1, MGMT, PD2, RAD54B, FLJ10979, IMPA1, HMGB2, PERQ1, KIAA0100, SLC13A5, or NUP43; more preferably KMO, SH3GL2, EDF1, MGMT, IMPA1, or SLC13A5.

Optionally, the above methods for identifying a potential therapeutic agent for treating HD further include administering the identified candidate agent to an animal model for HD and determining whether the agent prevents or reduces a symptom of HD in the animal model.

In some variations, the biological activity or characteristic associated with the toxicity of the huntingtin polypeptide is decreased cell viability relative to a cell that does not express the polypeptide, or the formation of inclusion bodies in the cell. The contacting of the first cell (and optionally the second cell) with the candidate agent can include, for example, transformation, culturing the cell in media containing the candidate agent, or administering the agent to a mammalian subject expressing the huntingtin polypeptide (e.g., to an animal model for HD).

In various embodiments, the biological activity associated with the with the wild-type protein is protease activity (e.g., KEX1); protein binding (e.g., CYK3, PAF1, VPS53, or UME-1); lipid metabolism (e.g., YDR287W, IMPA1); or vesicle-mediated transport (e.g., SH3GL2, MSO1, VPS53, VPS60, SNA2, YBR241C).

In specific variations, the wild-type protein and corresponding biological activity are any one of the following:
  BNA4 and hydroxylation of kynurenine to 3-hydroxykynurenine;
  BNA4 and interaction with GCS1;
  CYK3 and cytokinesis;
  CYK3 and association with BNR1;
  SH3GL2 and synaptic vesicle fission;
  MBF1 and transcriptional coactivation of Gcn4p;
  MGT1 and methyltransferase activity;
  MGT1 and O6-methylguanine DNA repair;
  PAF1 and association with RNA polymerase II;
  PAF1 and transcription initiation from a Pol II promoter;
  PAF1 and transcription elongation;

RDH54 and G2/M transition of mitotic cell cycle;
RDH54 and mitotic diploid-specific recombination and repair;
KEX1 and C-terminal Arg- or Lys-specific carboxypeptidase activity;
VPS53 and association with SAC2P and/or LUV1P;
VPS53 and protein sorting in the late Golgi;
YDR287W and hydrolysis of inositol-1-phosphate;
YDR287W and calcium signaling;
HSP104 and induced thermotolerance;
HSP104 and resolubilization of aggregates of denatured proteins;
HSP104 and [psi−] to [PSI+] prion conversion;
HSP104 and ethanol and acetaldehyde resistance;
NHP6B and DNA-binding activity;
NHP6B and DNA-bending activity;
NHP6B and transcription activation;
SMY2 and suppression of myo2-66 mutant when overexpressed;
SMY2 and suppression of sec22 mutant when overexpressed;
SMY2 and suppression of bet1 mutant when overexpressed;
SMY2 and suppression of sec16-3 mutant when overexpressed;
SMY2 and suppression of spt15 mutant when overexpressed;
SMY2 and suppression of yrb1-51 mutant when overexpressed;
PHO87 and phosphate uptake under high phosphate growth conditions;
MSL1 and association with U2 snRNA;
MSL1 and targeting of PRC1 to the vacuole;
UME-1 and repression of meiotic gene expression in mitotically-growing cells;
UME-1 and interaction with RPD3P and SIN3P;
UME-1 and negative regulation of transcription from a Pol II promoter;
BNA1 and 3-hydroxyanthranilate 3,4-dioxygenase activity;
YBR241C and hexose transport;
YBR241C and PRC1P vacuolar trafficking;
YDR459C and DNA binding;
NUP2 and nucleocytoplasmic transport;
NUP2 and loss of chromatin silencing;
RANBP2 and SUMO ligase activity;
YDJ1 and protein import into mitochondria;
YDJ1 and protein import into ER; or
YDJ1 and binding of unfolded ER proteins.

In yet another aspect, the present invention provides a method for detecting a change in expression of a human gene associated with a predisposition to Huntington's Disease. The method includes (1) obtaining biological samples having nucleic acids from a plurality of subjects having or at risk for developing HD, where the biological samples include nucleic acids; (2) analyzing the samples to determine an expression level of at least one of the following genes in the subjects: KMO, SH3GL2, EDF1, MGMT, PD2, RAD54B, PPGB, FLJ10979, IMPA1, SKD, HMGB2, PERQ1, KIAA0100, SLC13A5, SNRPA, NUP43, HAAO, SLC2A1, ZDHHC15, SEMG2, RANBP2, and DNAJA2; and (3) comparing the expression levels of the human gene in the subjects with the expression level of the human gene in a human subject not having or at risk for developing HD to determine whether a difference in expression of the human gene is correlated with a predisposition in a human having HD.

In still another aspect, the present invention provides a method of identifying a polymorphism, in a human gene, correlated with a predisposition in a human to developing a neurodegenerative disease (e.g., Huntington's Disease). The method includes (1) obtaining a plurality of biological samples having nucleic acids from a plurality of human subjects having or at risk for developing the neurodegenerative disease; (2) analyzing nucleic acids obtained from the biological samples to determine whether a polymorphism is present in at least one of the following human genes of the subjects: KMO, SH3GL2, EDF1, MGMT, PD2, RAD54B, PPGB, FLJ10979, IMPA1, SKD, HMGB2, PERQ1, KIAA0100, SLC13A5, SNRPA, NUP43, HAAO, SLC2A1, ZDHHC15, SEMG2, RANBP2, and DNAJA2; and (3) determining whether the mutation in the human gene in a plurality of subjects is correlated with the predisposition in a human to develop the neurodegenerative disease. The polymorphism can be, for example, a single nucleotide substitution. Further, in various embodiments, the polymorphism is in a promoter region, 5' untranslated region, coding region, intron, 3' untranslated region, or 3' untranscribed region of the human gene. Suitable methods for detecting the polymorphism include, e.g., sequencing genomic DNA segments containing at least a portion of the human gene, sequencing a cDNA encoding at least a portion of the human gene, restriction fragment length polymorphism analysis, allele-specific PCR, ligase chain reaction, or single-stranded length polymorphism.

DETAILED DESCRIPTION OF THE INVENTION

The present invention relates to methods for identifying agents that suppress toxicity of an amyloidogenic polypeptide. The methods are generally based, inter alia, on the present inventor's identification of wild-type genes that mediate the toxic effects of an amyloidogenic polypeptide expressed in a eukaryotic cell, whereby the absence of the wild-type gene from the eukaryotic cell suppresses cellular toxicity of the amyloidogenic polypeptide. The wild-type genes are particularly identified as mediating the toxic effects of an amyloidogenic neurotoxic polypeptide (hereinafter "neurotoxic polypeptide"). These wild-type genes are referred to herein as genes that enhance toxicity of a neurotoxic polypeptide. Agents that inhibit these genes, or their gene products, are identified by assaying for suppression of gene or encoded protein function in any of various screening or selection methods to identify potential therapeutic agents for the treatment of amyloidosis (amyloidogenic disease), particularly neurodegenerative disease such as, e.g., Huntington's Disease or Parkinson's Disease. The present invention also provides methods of identifying a polymorphism in, or changes in expression of, a gene associated with such amyloidogenic diseases.

I. Definitions

As used herein, the term "amyloidogenic polypeptide" refers to a protein, polypeptide, or peptide that is capable of forming or inducing the formation of protein aggregates or deposits, typically insoluble protein fibrils, either intracellular or extracellularly, or that contains a motif or domain involved in a molecular cascade involved in the formation of such protein aggregates or deposits. Amyloidogenic polypeptides are involved in the etiology and pathology and various amyloidogenic disease, including, e.g., neurodegenerative diseases (see, e.g., Ross and Poirier, *Nature Medicine* 10 (Supplement):S10-S17, 2004) as well as systemic diseases.

The term "neurotoxic polypeptide" refers to an amyloidogenic polypeptide that is neurotoxic when expressed in humans. Neurotoxic effects can be caused by a variety of cellular processes typically involved in amyloidosis, including protein misfolding, aggregation, mis-localization, accumulation, and/or deposition (such as inclusion or Lewy body formation). In humans, a neurotoxic effect can lead to, e.g., neurodegeneration, which can result in a loss of motor control, memory loss, dementia, and ultimately death. Typical neurotoxic polypeptides include those associated with Huntington's Disease and Parkinson's Disease, such as, for example, huntingtin polypeptide and α-synuclein, respectively, as well as fragments thereof. Other suitable neurotoxic polypeptides are associated with neurotoxic effects in neurodegenerative diseases such as spinocerebellar ataxias, Alzheimer's disease, or the like.

As used herein, "candidate agent" refers to any agent with a potential to structurally interact with biomolecules, particularly proteins, through non-covalent interactions, such as, for example, through hydrogen bonds, ionic bonds, van der Waals attractions, or hydrophobic interactions. Many types of candidate agents can be screened by the methods according to the present invention. Suitable candidate agents include, for example, small molecules, nucleic acids, peptides, peptidomimetics, synthetic compounds, and/or natural compounds.

As used herein, the term "potential therapeutic agent" refers to an agent that can reduce, alleviate, prevent, or reverse the toxic effects of a neurotoxic polypeptide in a cell, as determined, e.g., by the methods described herein. Such agents will be recognized as having the potential in vivo to reduce, alleviate, prevent, or reverse at least one symptom of a neurodegenerative disease associated with the neurotoxic polypeptide. A "potential therapeutic agent" as defined herein need not actually exhibit therapeutic efficacy in vivo: since candidate agents identified as having substantial activity on cells in vitro are useful, e.g., for the elucidation of structure-activity relationships associated with suppression of toxicity in cells, these agents can be used (e.g., as lead compounds) for the further development of a therapeutic agent that substantially retains the ability (or has an improved ability) to inhibit toxicity of the neurotoxic polypeptide in a cell, but which also has, relative to the originally identified agent, other properties better suited for in vivo use (e.g., increased stability, increased cellular uptake, or other properties which provide for a more favorable pharmacokinetic and/or pharmacodynamic profile).

In reference to a wild-type gene, the phrase "enhance toxicity of a neurotoxic polypeptide," as used herein, means that the absence of the wild-type in a eukaryotic cell (i.e., a null mutant or deletion of the gene) significantly suppresses the toxicity of a neurotoxic polypeptide expressed in the cell, relative to a congenic cell in which the wild-type gene is expressed.

As used herein, the phrase "biological activity associated with toxicity of a neurotoxic polypeptide," in reference to a eukaryotic cell, refers to any biochemical or cellular process or characteristic that has a measurable correlative relationship with toxicity of the neurotoxic polypeptide. Typical biological activities associated with toxicity of a neurotoxic polypeptide include, for example, retardation of cell growth, decrease in cell viability, formation of inclusion bodies, or cellular changes associated with apoptosis (e.g., DNA fragmentation, loss of membrane integrity, and the like).

As used herein, the phrase "biological activity associated with a protein," refers to any in vitro biochemical process, or biochemical or cellular process or characteristic when the protein is expressed in a cell, that is mediated by the protein or has a measurable correlative relationship with the normal function of the protein. Biological activities associated with a protein can include, for example, an enzymatic activity mediated by the protein itself (e.g., kinase activity, phosphatase activity, protease activity (e.g., ubiquitin-specific protease activity)); association with or binding of one or more other biomolecules (e.g., proteins, lipoproteins, DNA, RNA, and the like); intracellular activities such as, for example, transcription or gene expression, cell cycle transitions (e.g., G2/M transition), vesicle-mediated transport, or intracellular signaling (e.g., calcium signaling, sphingolipid-mediated signaling, or signaling through the MAP kinase pathway); or any detectable cellular phenotype associated with normal function of the protein (e.g., salt tolerance, suppression of other characterized mutations, protection from apoptosis, and the like).

As used herein, the term "substantial decrease" means a measurable decrease, relative to a reference value, that is statistically significant. In certain embodiments, a substantial decrease, expressed as a percentage decrease relative to a reference value (e.g., a measured level of a biological activity for a control cell or protein) is a decrease of at least 10%, at least 20%, at least 30%, at least 40%, or at least 50%. For example, in the context of determining the level of a biological activity in a first cell relative to that in a second cell, each in the presence of a candidate agent, the level of the biological activity for each cell in the presence of the agent are measured and compared and, if the measured level for the first cell is significantly less than the measured level for the second cell, then the first cell exhibits a substantial decrease in the biological activity relative to the second cell.

As used herein, the term "nucleic acid" generally refers to at least one molecule or strand of DNA, RNA, or a derivative or mimic thereof, comprising at least one base, such as, for example, a naturally occurring purine or pyrimidine base found in DNA (e.g., adenine "A," guanine "G," thymine "T," and cytosine "C") or RNA (e.g., A, G, uracil "U," and C). The term "nucleic acid" encompasses the terms "oligonucleotide" and "polynucleotide." The term "oligonucleotide" refers to at least one molecule of between about 3 and about 100 bases in length. The term "polynucleotide" refers to at least one molecule of greater than about 100 bases in length. These definitions generally refer to at least one single-stranded molecule, but in specific embodiments also encompass at least one additional strand that is partially, substantially, or fully complementary to the at least one single-stranded molecule. Thus, a nucleic acid can encompass at least one double-stranded molecule that comprises one or more complementary strand(s) or "complement(s)" of a particular sequence comprising a strand of the molecule.

As used herein, the term "promoter" refers to a control sequence that controls the initiation and rate of transcription. A promoter can contain genetic elements at which regulatory proteins and molecules bind, such as RNA polymerase and other transcription factors, to initiate the specific transcription of a nucleic acid sequence. A promoter can also include an enhancer. The phrases "operatively positioned," "operatively linked," and "operatively associated" mean that a promoter is in a correct functional location and/or orientation in relation to a nucleic acid sequence to control transcriptional initiation and/or expression of a downstream sequence.

The term "gene" refers to a nucleic acid that is transcribed. As used herein, a "gene segment" is a nucleic acid segment of a gene. A gene can include regulatory sequences involved in transcription, or message production or composition. In particular embodiments, the gene comprises transcribed sequences that encode a protein, polypeptide, or peptide. In keeping with the terminology described herein, an "isolated gene" can comprise transcribed nucleic acid(s), regulatory sequences, coding sequences, or the like, isolated substantially away from other such sequences, such as other naturally occurring genes, regulatory sequences, polypeptide or peptide encoding sequences, etc. In this respect, the term "gene" is used for simplicity to refer to a nucleic acid comprising a nucleotide sequence that is transcribed, and the complement thereof. In particular aspects, the transcribed nucleotide sequence comprises at least one functional protein, polypeptide, and/or peptide encoding unit. As will be understood by those in the art, this functional term "gene" includes genomic sequences, RNA or cDNA sequences, or smaller engineered nucleic acid segments, including nucleic acid segments of a non-transcribed part of a gene, including but not limited to the non-transcribed promoter or enhancer regions of a gene. Smaller engineered gene nucleic acid segments can express, or can be adapted to express using nucleic acid manipulation technology, proteins, polypeptides, domains, peptides, fusion proteins, mutants and/or such like. Thus, a "truncated gene" refers to a nucleic acid sequence that is missing a stretch of contiguous nucleic acid residues that encode a portion of a full-length protein or polypeptide. For example, a truncated gene may not contain the nucleic acid sequence for the N-terminal region of the protein or polypeptide.

As used herein, "wild-type gene" refers to a sequence of nucleic acid, at a genetic locus in the genome of an organism, that encodes a gene product which performs the normal function of the gene product encoded by a naturally occurring nucleotide sequence corresponding to the genetic locus. A genetic locus can have more than one sequence or allele in a population of individuals, and the term "wild-type" encompasses all such naturally-occurring alleles that encode a gene product performing the normal function. "Wild-type" also encompasses gene sequences that are not necessarily naturally occurring, but that still encode a gene product with normal function (e.g., genes having silent mutations or encoding proteins with conservative substitutions).

The term "wild-type polypeptide" or "wild-type protein" refers to a protein, polypeptide, or peptide encoded by a wild-type gene. A genetic locus can have more than one sequence or allele in a population of individuals, and the term "wild-type" encompasses all such naturally-occurring alleles that encode a gene product performing the normal function. In addition to naturally-occurring amino acid sequence variants having normal protein function, wild-type polypeptides include derivatives altered by substitution, addition or deletion of one or more amino acid residues that provide for functionally active molecules. Polypeptide derivatives include, but are not limited to, those containing as a primary amino acid sequence of all or part of the amino acid sequence of a polypeptide, including altered sequences in which one or more functionally equivalent amino acid residues (e.g., a conservative substitution) are substituted for residues within the sequence.

As used herein, the term "polymorphic" means that multiple variants exists (i.e., two or more alleles exist) at a genetic locus in the individuals of a population. The term "polymorphism" refers to a difference between two alleles. The term "mutant" refers to a gene having a change in the sequence of a gene or its encoded gene product (e.g., a protein, polypeptide, or peptide), as a result of which the gene product does not perform a function associated with the wild-type gene product. For example, a huntingtin polypeptide having an expanded polyQ region is a mutant. Similarly, a null allele can be a mutant gene. A mutant gene can also contain one or more missense, nonsense, and/or frameshift mutations.

As used herein, a "homolog" of a first gene refers to a second, different gene that is substantially identical to the first gene, or that encodes a gene product that is substantially identical to the gene product encoded by the first gene. An "ortholog" of a first gene refers to a second gene from a different organism that is substantially identical to the first gene, or that encodes a gene product that is substantially identical or substantially identical to the gene product encoded by the first gene.

As used herein, "percentage of sequence identity" is determined by comparing two optimally aligned sequences over a comparison window, wherein the portion of the sequence in the comparison window can comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of nucleotides or amino acid residues that are the same (e.g., 60% identity, optionally 65%, 70%, 75%, 80%, 85%, 90%, or 95% identity over a specified region), when compared and aligned for maximum correspondence over a comparison window, or designated region as measured using one of the following sequence comparison algorithms or by manual alignment and visual inspection. Sequences are "substantially identical" to each other if they are at least 20%, at least 25%, at least 30%, at least 35%, at least 40%, at least 45%, at least 50%, or at least 55% identical. These definitions also refer to the complement of a test sequence. Optionally, the identity exists over a region that is at least about 50 nucleotides in length, or more typically over a region that is 100 to 500 or 1000 or more nucleotides in length.

The terms "similarity" or "percent similarity," in the context of two or more polypeptide sequences, refer to two or more sequences or subsequences that have a specified percentage of amino acid residues that are either the same or similar as defined by a conservative amino acid substitutions (e.g., 60% similarity, optionally 65%, 70%, 75%, 80%, 85%, 90%, or 95% similar over a specified region), when compared and aligned for maximum correspondence over a comparison window, or designated region as measured using one of the following sequence comparison algorithms or by manual alignment and visual inspection. Sequences are "substantially similar" to each other if they are at least 20%, at least 25%, at least 30%, at least 35%, at least 40%, at least 45%, at least 50%, or at least 55% similar to each other. Optionally, this similarly exists over a region that is at least about 50 amino acids in length, or more typically over a region that is at least about 100 to 500 or 1000 or more amino acids in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities or similarities for the test sequences relative to the reference sequence, based on the program parameters.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, for example, by the local homology algorithm of Smith and Waterman (*Adv. Appl. Math.* 2:482 (1970)), by the homology alignment algorithm of Needleman and Wunsch (*J. Mol. Biol.* 48:443 (1970)), by the search for similarity method of Pearson and Lipman (*Proc. Natl. Acad. Sci. USA* 85:2444 ((1988)), by computerized implementations of these algorithms (e.g., GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng and Doolittle (*J. Mol. Evol.* 35:351-360 (1987)). The method used is similar to the method described by Higgins and Sharp (CABIOS 5:151-153 (1989)). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package (e.g., version 7.0 (Devereaux et al., *Nuc. Acids Res.* 12:387-95 (1984)).

Another example of an algorithm that is suitable for determining percent sequence identity and sequence similarity are the BLAST and BLAST 2.0 algorithms, which are described in Altschul et al. (*Nuc. Acids Res.* 25:3389-402 (1977)), and Altschul et al. (*J. Mol. Biol.* 215:403-10 (1990)), respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin and Altschul, *Proc. Natl. Acad. Sci. USA* 90:5873-87). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, typically less than about 0.01, and more typically less than about 0.001.

Gene homologs and orthologs can also be identified using the HomoloGene resource of NCBI. A homolog or ortholog of a first gene can encode a gene product that has the same or a similar function as the gene product encoded by the first gene. Another indication that two nucleic acid sequences or polypeptides are orthologs is that the heterologous gene can complement (e.g., rescue) a null allele of the endogenous gene in a eukaryotic cell expression system.

II. Identification of Potential Therapeutic Agents or Lead Compounds for Treatment of Neurodegenerative Disease A. Eukaryotic Systems for Expressing Neurotoxic Polypeptides and Related Methods In one aspect, eukaryotic cell expression systems and methods are provided for screening candidate agents to identify those agents that reduce toxicity of the neurotoxic polypeptide. The methods utilize a first eukaryotic expression system to express (1) a neurotoxic polypeptide, the expression of which is toxic to the cell, and (2) a wild-type gene that enhances the toxicity of the neurotoxic polypeptide. Also utilized is a second eukaryotic expression system to express the neurotoxic polypeptide, but not the wild-type gene. A eukaryotic cell of each expression system (a "first cell" and "second cell," respectively) is contacted with a candidate agent and the cells are assayed for a biological activity associated with the toxicity of the neurotoxic polypeptide. Suitable candidate agents include, for example, nucleic acids, proteins, polypeptides, peptide, natural agents, synthetic agents, and the like. If the first cell (a) exhibits a substantial decrease of the biological activity, relative to a control cell (expressing the neurotoxic polypeptide and wild-type gene) that has not been contacted with the agent, and (b) exhibits a lack of a substantial decrease of the biological activity relative to the second cell, then the candidate agent is identified as a potential therapeutic for the treatment of a neurodegenerative disease associated with the neurotoxic polypeptide.

The neurotoxic polypeptide can be full length, substantially full-length, or a functionally equivalent form of the neurotoxic polypeptide. Alternatively, the neurotoxic polypeptide can be a truncated polypeptide or a polypeptide with one or more internal deletions. The neurotoxic polypeptide is typically derived from a human source. In specific embodiments, the neurotoxic polypeptide is a human huntingtin polypeptide, the polypeptide encoded by exon one of human huntingtin gene, or human α-synuclein. In additional embodiments, the neurotoxic polypeptide can be a non-human, mammalian homolog or ortholog of a human neurotoxic polypeptide, or a fragment thereof. In some embodiments, the neurotoxic polypeptide has an expanded polyQ region. In the example of a huntingtin polypeptide encoded by exon 1, the polypeptide typically includes the first 17 amino acids of exon 1 followed by an expanded polyQ region. In certain variations, the huntingtin polypeptide is about 68 amino acids in length, excluding polyQ repeats. The polyQ region, which is typically about 25 glutamine residues in length in wild-type huntingtin, is expanded in mutant huntingtin polypeptides associated with neurotoxicity. For example, mutant huntingtin genes can encode a mutant huntingtin polypeptide having at least 37, at least 45, at least 70, or at least 100 glutamine residues in a polyQ region. In particularly suitable huntingtin polypeptides with an expanded polyQ region, the number of polyQ repeats is at least about 45 glutamine residues in length. In one specific embodiment, the huntingtin polypeptide having an expanded polyQ repeat includes the first 17 amino acids of exon 1 followed by 103 glutamine residues. (See, e.g., Meriin et al., *J. Cell. Biol.* 157:997-1004 (2002).)

The sequence of a neurotoxic polypeptide can also be modified by amino acid substitutions, replacements, insertions, deletions, truncations, and other modifications. Typically such modifications can be used to prepare mimics of biologically-occurring polypeptides or to generate suitable targets for screening.

For example, certain amino acids can be substituted for other amino acids in a polypeptide without appreciable loss of neurotoxicity (e.g., ability to aggregate). Such changes can be conservative changes. The following eight groups each contain amino acids that are regarded conservative substitutions for one another:

1) Alanine (A) and Glycine (G);
2) Aspartic acid (D) and Glutamic acid (E);
3) Asparagine (N) and Glutamine (Q);
4) Arginine (R) and Lysine (K);
5) Isoleucine (I), Leucine (L), Methionine (M) and Valine (V);
6) Phenylalanine (F), Tyrosine (Y) and Tryptophan (W);
7) Serine (S) and Threonine (T); and
8) Cysteine (C) and Methionine (M) (see, e.g., Creighton, *Proteins*, W.H. Freeman and Co., New York (1984)).

In designing modified polypeptides, the hydropathic index of amino acids can be considered (see, e.g., Kyte and Doolittle, *J. Mol. Biol.* 157:105-32 (1982)). Amino acid substitutions can also be made on the basis of hydrophilicity.

A neurotoxic polypeptide also can be a fusion protein comprising a neurotoxic polypeptide or a fragment thereof joined at its N- or C-terminus to a second polypeptide. The second polypeptide can be, for example, an epitope, a selectable protein, an enzyme, or the like. For example, the second polypeptide can be β-galactosidase, green fluorescent protein (GFP), FLAG, Myc, or the like. In specific embodiments, a neurotoxic polypeptide such as, for example, α-synuclein or a huntingtin polypeptide (e.g., a huntingtin polypeptide containing the first 17 amino acids of exon 1 followed by 103 glutamine residues) is fused in frame with GFP at the C-terminus and with FLAG at the N-terminus. (See, e.g., Meriin et al., supra.)

A variety of eukaryotic cell expression systems can be used in the methods according to the present invention. A suitable eukaryotic cell expression system is one in which expression of the neurotoxic polypeptide in a suitable genetic background causes toxicity. One model eukaryotic organism, yeast, provides a well established system for genetic and chemical screening. Many genes can be studied in yeast because they are non-essential under certain growth conditions. In addition, homologs and orthologs of yeast genes can be studied in yeast because such homologs and orthologs often have overlapping functions with the yeast genes, allowing deletion or inactivation of the yeast gene.

Suitable yeast strains which can be used in the context of the present invention include, for example, *Saccharomyces cerevisiae, Saccharomyces uvae, Saccharomyces kluyveri, Schizosaccharomyces pombe, Saccharomyces uvarum, Kluyveromyces lactis, Hansenula polymorpha, Pichia pastoris, Pichia methanolica, Pichia kluyveri, Yarrowia lipolytica, Candida* species such as *Candida utilis* or *Candida cacaoi, Geotrichum* species such as *Geotrichum fermentans*, and the like. In a typical embodiment, the yeast strain is *Saccharomyces cerevisiae.*

Other suitable eukaryotic cell expression systems can include, for example, rat, mouse, *Drosophila*, or *C. elegans*. The eukaryotic cell expression system can be another non-human animal, insect, or lower model system. A suitable eukaryotic cell expression system also can be human cells or cells isolated from such a non-human eukaryotic organism, such as, for example, rat, mouse, *Drosophila*, or *C. elegans* cells cultured in vitro. The eukaryotic cell expression system can be genetically engineered to express a neurotoxic polypeptide. For example, *Drosophila* can be genetically engineered to express a neurotoxic polypeptide that causes toxicity in a suitable genetic background. Alternatively, the system can express an endogenous neurotoxic polypeptide that causes toxicity in a suitable genetic background.

The eukaryotic cell of the eukaryotic cell expression system (e.g., a yeast strain) optionally includes alleles of, or mutations in, genes that facilitate uptake or increase permeability of a candidate agent(s), and/or alleles of, or mutations in, genes that reduce or prevent metabolism of a candidate agent(s). For example, in some embodiments, a yeast strain includes mutations in one or more of the yeast genes erg6, pdr1, and/or pdr3, which affect membrane efflux pumps and may increase permeability of candidate agents.

The genetic background of the first eukaryotic cell expression system is one in which expression of the neurotoxic polypeptide causes toxicity (hereinafter referred to as a "suitable genetic background"). The neurotoxic polypeptide is expressed in the cell having a suitable genetic background at levels sufficient to manifest in the cell at least one biological activity or characteristic associated with a toxic phenotype. In certain embodiments, the suitable genetic background includes the lack of expression of a second wild-type gene, the absence of which causes or enhances toxicity of the neurotoxic polypeptide expressed in the cell (see, e.g., co-pending U.S. Patent Application No. 60/527,215). The toxic phenotype is typically manifested by a reduced growth rate, growth inhibition and/or cell death. Other suitable biological activities or characteristics associated with toxicity of the neurotoxic polypeptide include, e.g., the formation of inclusion bodies in the cell or cellular or biochemical changes associated with apoptosis. In certain expression systems, expression of the neurotoxic polypeptide causes neurotoxicity.

The second eukaryotic cell, which lacks the wild-type gene that enhances toxicity of the neurotoxic polypeptide, is congenic to the first cell. Thus, toxicity of the neurotoxic polypeptide will be suppressed in the second cell relative to the first cell. Typically, the lack in the second eukaryotic cell of the wild-type gene is due to a null mutation, such as a deletion of all or part of the gene. The absence of the wild-type gene also can be due to a mutation causing a partial loss of function of, a change of function of, or acquisition of a new function, by the gene and its gene product.

In additional variations, an endogenous wild-type gene, enhancing toxicity of the neurotoxic polypeptide, can be inactivated (e.g., a null allele) in each of the first and second eukaryotic cells, and the first cell can express a homolog or ortholog of the endogenous wild-type gene. The homolog or ortholog can be, for example, a human ortholog of the endogenous gene associated with toxicity, as described herein. The homolog or ortholog also can be a mutant, such as a mutant human gene which causes or enhances toxicity in the cell expression system, or neurotoxicity in humans. Particularly suitable are yeast strains in which the endogenous wild-type gene is inactivated and in which a human ortholog of the wild-type gene is expressed.

As discussed above, a eukaryotic cell of the first eukaryotic cell expression system expresses, and the corresponding second eukaryotic system lacks, at least one wild-type gene that enhances toxicity of the neurotoxic polypeptide. For example, in the context of a huntingtin polypeptide expressed in a yeast system, the first yeast cell expresses and the second yeast cell lacks at least one of the following wild-type yeast genes: BNA4, CYK3, DEF1, ECM37, MBF1, MGT1, MSO1, PAF1, RDH54, RXT3, SNA2, KEX1, VPS53, YBR016W, YDR287W, YER185W, YLR278C, YMR082C, HSP104, NHP6B, SMY2, YLR454W, PHO87, RNQ1, BFR1, MSL1, UME-1, YIR003W, YMR244C-A, ARG7, YCL005W, BNA1, VPS60, YBR241C, YDR459C, YMR075C-A, YMR086W, COX5B, NUP2, and YDJ1. Particularly suitable yeast genes include BNA4, CYK3, DEF1, ECM37, MBF1, MGT1, MSO1, PAF1, RDH54, RXT3, SNA2, VPS53, YBR016W, YDR287W, YER185W, YLR278C, YMR082C, NHP6B, SMY2, YLR454W, PHO87, RNQ1, BFR1, UME-1, YIR003 W, YMR244C-A, and ARG7. In certain preferred variations, the yeast gene is BNA4, CYK3, DEF1, MBF1, MGT1, PAF1, RDH54, VPS53, YBR016W, YDR287W, NHP6B, SMY2, YLR454W, PHO87, RNQ1, UME-1, or YMR244C-A, more preferably BNA4, CYK3, MBF1, MGT1, YDR287W, or PHO87. In certain embodiments, the yeast gene is not DEF1, YBR016W, RNQ1, or YIR003W.

In other embodiments in which a huntingtin polypeptide is expressed in a yeast system, the first cell expresses and the second cell lacks at least one of the following wild-type yeast genes: BNA4, DEF1, MBF1, MSO1, PAF1, RDH54, SNA2, KEX1, YBR016W, YDR287W, YLR278C, YMR082C, NHP6B, YLR454W, MSL1, YIR003W, YMR244C-A, YMR086W, and NUP2. BNA4, DEF1, MBF1, PAF1, RDH54, KEX1, YBR016W, YDR287W, NHP6B, YLR454W, MSL1, YIR003W, YMR086W, and NUP2 are particularly suitable.

In further variations in the context of a huntingtin polypeptide, the first eukaryotic cell expresses, and the second eukaryotic cell lacks, an ortholog of at least one of the yeast genes set forth above. Suitable eukaryotic expression systems for expression (and corresponding deletion) of orthologs of these yeast genes include, for example, rat, mouse, *Drosophila*, or *C. elegans* expression systems. In certain embodiments, the first eukaryotic cell expresses and the second eukaryotic cell lacks at least one ortholog of the following wild-type genes: BNA4, CYK3, DEF1, MBF1, MGT1, PAF1, RDH54, KEX1, VPS53; YBR016W, YDR287W, HSP104, NHP6B, SMY2, YLR454W, PHO87, RNQ1, MSL1, UME-1, YIR003W, BNA1, YBR241C, YDR459C, YMR086W, NUP2, and YDJ1. Orthologs of BNA4, CYK3, DEF1, MBF1, MGT1, PAF1, RDH54, VPS53, YBR016W, YDR287W, NHP6B, SMY2, YLR454W, PHO87, RNQ1, UME-1, and YMR244C-A are particularly suitable. In one preferred embodiment, the wild-type gene is an ortholog of BNA4, CYK3, MBF1, MGT1, YDR287W, or PHO87. In certain embodiments, the wild-type gene is not an ortholog of DEF1, YBR016W, RNQ1, or YIR003W. In yet another variation, the wild-type gene is an ortholog of BNA4, DEF1, MBF1, PAF1, RDH54, KEX1, YBR016W, YDR287W, NHP6B, YLR454W, MSL1, YIR003W, YMR086W, or NUP2.

For example, in certain embodiments, the first cell expresses, and the second cell lacks, a human ortholog of at least one of the yeast genes, set forth above, that enhance toxicity of a huntingtin polypeptide comprising an expanded polyQ repeat (also referred to herein as "polyQ toxicity"). Table 1, infra, lists exemplary human orthologs of yeast genes that enhance polyQ toxicity.

TABLE 1

Human orthologs of yeast genes that enhance polyQ toxicity

| Yeast Gene | Human Ortholog(s) (% Homology) |
|---|---|
| BNA4 | KMO (38%) |
| CYK3 | SH3GL2 (39%) |
| DEF1 | FLJ39117 (25%); TXNDC2 (24%) |
| MBF1 | EDF1 (45%) |
| MGT1 | MGMT (41%) |
| PAF1 | PD2 (22%) |
| RDH54 | RAD54B (37%) |
| KEX1 | PPGB (27%) |
| VPS53 | FLJ10979 (22%) |
| YBR016W | SS18 (40%); TXNDC2 (24%) |
| YDR287W | IMPA1 (41%) |
| HSP104 | SKD (34%) |
| NHP6B | HMGB2 (42%) |
| SMY2 | PERQ1 (39%) |
| YLR454W | KIAA0100 (42%) |
| PHO87 | SLC13A5 (22%) |
| RNQ1 | FLJ39117 (26%) |
| MSL1 | SNRPA (33%) |
| UME-1 | NUP43 (22%) |
| YIR003W | TXNDC2 (21%) |
| BNA1 | HAAO (42%) |
| YBR241C | SLC2A1 (30%) |
| YDR459C | ZDHHC15 (24%) |
| YMR086W | SEMG2 (21%) |
| NUP2 | RANBP2 (22%) |
| YDJ1 | DNAJA2 (48%) |

In some variations, in the context of a huntingtin polypeptide in which the cell expression system comprises ex vivo human cells, the first cell expresses and the second cell lacks at least one of the following wild-type genes: KMO, SH3GL2, FLJ39117, TXNDC2, EDF1, MGMT, PD2, RAD54B, PPGB, FLJ10979, SS18, IMPA1, SKD, HMGB2, PERQ1, KIAA0100, SLC13A5, FLJ39117, SNRPA, NUP43, HAAO, SLC2A1, ZDHHC15, SEMG2, RANBP2, and DNAJA2. Particularly suitable wild-type genes for ex vivo expression in human cells include KMO, SH3GL2, FLJ39117, TXNDC2, EDF1, MGMT, PD2, RAD54B, FLJ10979, SS18, IMPA1, HMGB2, PERQ1, KIAA0100, SLC13A5, and NUP43. For example, in one preferred embodiment, the human wild-type gene is KMO, SH3GL2, EDF1, MGMT, IMPA1, or SLC13A5. In some embodiments, the human wild-type gene is not FLJ39117, TXNDC2, or SS18. In other embodiments, the first cell expresses and the second cell lacks at least one of KMO, TXNDC2, EDF1, PD2, RAD54B, PPGB, SS18, IMPA1, HMGB2, KIAA0100, SNRPA, SEMG2, and RANBP2.

In the context of an α-synuclein polypeptide expressed in a yeast system, the first yeast cell expresses and the second yeast cell lacks at least one of the following wild-type yeast genes: VTS1, LPH17, YIM1, UBP2, VAM3, BUL1, SAL6, YOR138C, VPS30, RAV1, VPS38, SCP160, KAR5, YJR111C, YAP3, HAL9, YHL044W, YKL077W, LHS1, YPK1, UBP12, VPS13, YCL005W, YHM1, PUF4, YER030W, YBL083C, GIM4, YCL075W, MRPL13, HDA1, YBR027C, APT2, PMD1, GIM5, DHH1, BUD31, SFL1, FIG4, HSL1, PPG1, YCK2, SSK22, SPL2, PKH1, KNS1, SYT1, YPT53, YPS1, YPS3, DOA1, BRE5, YDR119W, YBT1, PDR5, and PDR16. Particularly suitable yeast genes include VTS1, UBP2, VAM3, VPS38, SCP160, YAP3, HAL9, YKL077W, YPK1, YBL083C, MRPL13, APT2, FIG4, and DOA1. In a preferred variation, the yeast gene is VTS1, UBP2, VAM3, SCP160, or YPK1.

In other embodiments in which an α-synuclein polypeptide is expressed in a yeast system, the first cell expresses and the second cell lacks at least one of the following wild-type yeast genes: VTS1, LPH17, YIM1, UBP2, VAM3, BUL1, SAL6, YOR138C, VPS30, RAV1, VPS38, SCP160, KAR5, YJR111C, YAP3, HAL9, YHL044W, YKL077W, LHS1, YPK1, UBP12, VPS13, YCL005W, YHM1, PUF4, YER030W, YBL083C, GIM4, YCL075W, MRPL13, HDA1, YBR027C, APT2, PMD1, GIM5, DHH1, BUD31, and SFL1. VTS1, LPH17, YIM1, UBP2, VAM3, SAL6, VPS30, RAV1, SCP160, LHS1, YPK1, UBP12, VPS13, YHM1, PUF4, GIM4, HDA1, APT2, PMD1, GIM5, DHH1, BUD31, and SFL1 are particularly suitable.

In other variations in the context of an α-synuclein polypeptide, the first eukaryotic cell expresses, and the second eukaryotic cell lacks, an ortholog of at least one of the yeast genes set forth above. Suitable eukaryotic cell expression systems include, for example, rat, mouse, *Drosophila*, and *C. elegans*. In certain embodiments, the first eukaryotic cell expresses and the second eukaryotic cell lacks at least one ortholog of the following wild-type genes: VTS1, LPH17, YIM1, UBP2, VAM3, SAL6, VPS30, RAV1, SCP160, LHS1, YPK1, UBP12, VPS13, YHM1, PUF4, YER030W, GIM4, HDA1, APT2, PMD1, GIM5, DHH1, BUD31, SFL1, FIG4, HSL1, PPG1, YCK2, SSK22, PKH1, KNS1, SYT1, YPT53, YPS1, YPS3, DOA1, BRE5, YBT1, PDR5, and PDR16. Particularly suitable are orthologs of VTS1, UBP2, VAM3, VPS38, SCP160, YAP3, HAL9, YKL077W, YPK1, YBL083C, MRPL13, APT2, FIG4, and DOA1. In one preferred embodiment, the wild-type gene is an ortholog of VTS1, UBP2, VAM3, SCP160, or YPK1. In yet another variation, the wild-type gene is an ortholog of VTS1, LPH17, YIM1, UBP2, VAM3, SAL6, VPS30, RAV1, SCP160, LHS1, YPK1, UBP12, VPS13, YHM1, PUF4, GIM4, HDA1, APT2, PMD1, GIM5, DHH1, BUD31, or SFL1.

For example, in certain embodiments, the first cell expresses, and the second cell lacks, a human ortholog of at least one of the yeast genes, set forth above, that enhance toxicity of an α-synuclein polypeptide (also referred to herein as "α-synuclein toxicity"). Table 2, infra, lists exemplary human orthologs of yeast genes that enhance α-synuclein toxicity.

TABLE 2

Human orthologs of yeast genes that enhance
α-synuclein toxicity

| Yeast Gene | Human Ortholog(s) (% Homology) |
|---|---|
| VTS1 | FLJ10211 (33%) |
| LPH17 | ADCK2 (31%) |
| YIM1 | RTN4IP1 (26%) |
| UBP2 | USP28 (22%) |
| VAM3 | STX16 (27%) |
|  | STX1B2 (24%) |
| SAL6 | PPP1CB (58%) |
| VPS30 | BECN1 (29%) |
| RAV1 | DMXL1 (26%) |
|  | RC3 (26%) |
| SCP160 | HDLBP (22%) |
| LHS1 | HYOU1 (26%) |
| YPK1 | SGK2 (51%) |
| UBP12 | USP15 (28%) |
| VPS13 | VPS13A (23%) |
| YHM1 | SLC25A15 (29%) |
| PUF4 | PUM2 (29%) |
| GIM4 | PFDN2 (39%) |
| HDA1 | HDAC6 (39%) |
| APT2 | APRT (40%) |
| PMD1 | DSPP (22%) |
| GIM5 | PFDN5 (37%) |
| DHH1 | DDX6 (66%) |
| BUD31 | G10 (51%) |
| SFL1 | HSF4 (49%) |
| FIG4 | SAC3 (38%) |
| HSL1 | STK29 (38%) |
|  | KIAA1811 (38%) |
| PPG1 | PPP4C (56%) |
| YCK2 | CSNK1G2 (51%) |
| SSK22 | MAP3K4 (36%) |
|  | MAP3K5 (37%) |
| PKH1 | PDPK1 (46%) |
| KNS1 | CLK1 (35%) |
| SYT1 | BIG1 (28%) |
| YPT53 | RAB5C (52%) |
|  | RAB5A (53%) |
| YPS1 | PGC (27%) |
| YPS3 | PGC (30%) |
| DOA1 | PLAA (31%) |
| BRE5 | G3BP2 (23%) |
| YBT1 | ABCC1 (32%) |
| PDR5 | ABCG2 (30%) |
| PDR16 | PTPN9 (22%) |

In particular variations, in the context of an α-synuclein polypeptide in which the eukaryotic cell expression system comprises ex vivo human cells, the first cell expresses and the second cell lacks at least one of the following wild-type genes: FLJ10211, ADCK2, RTN4IP1, USP28, STX16, STX1B2, PPP1CB, BECN1, DMXL1, RC3, HDLBP, HYOU1, SGK2, USP15, VPS13A, SLC25A15, PUM2, PFDN2, HDAC6, APRT, DSPP, PFDN5, DDX6, G10, HSF4, SAC3, STK29, KIAA1811, PPP4C, CSNK1G2, MAP3K4, MAP3K5, PDPK1, CLK1, BIG1, RAB5C, RAB5A, PGC, PLAA, G3BP2, ABCC1, ABCG2, and PTPN9. Particularly suitable wild-type genes for ex vivo expression in human cells include FLJ10211, USP28, STX16, STX1B2, HDLBP, and SGK2. In other embodiments, the first cell expresses and the second cell lacks at least one of FLJ10211, ADCK2, RTN4IP1, USP28, STX16, PPP1CB, BECN1, DMXL1, RC3, HDLBP, HYOU1, SGK2, USP15, VPS13A, SLC25A15, PUM2, PFDN2, HDAC6, APRT, DSPP, PFDN5, DDX6, G10, and HSF4.

The eukaryotic cell expression system according to the present invention expresses a neurotoxic polypeptide. Typically, a nucleic acid encoding the neurotoxic polypeptide is introduced into at least one cell of the expression system. For example, a nucleic acid encoding a neurotoxic polypeptide can be introduced into a yeast cell. The nucleic acid can be introduced, for example, as a linear nucleic acid fragment or as part of a replicating or integrating vector. The nucleic acid can encode a full-length, substantially full-length, or functionally equivalent form of the neurotoxic polypeptide. Alternatively, the neurotoxic polypeptide can be a truncated polypeptide or a polypeptide with one or more internal deletions. The nucleic acid encoding the neurotoxic polypeptide is typically derived from a human source. In additional embodiments, the nucleic acid encoding the neurotoxic polypeptide can encode a non-human, mammalian homolog of the human neurotoxic polypeptide. In exemplary embodiments, the nucleic acid encoding a neurotoxic polypeptide encodes a human huntingtin or α-synuclein polypeptide, which can be introduced into the yeast cell by transformation.

Nucleic acid can be obtained from any suitable source. Non-limiting examples of synthetic nucleic acid, particularly a synthetic oligonucleotide, include a nucleic acid made by in vitro chemical synthesis using phosphotriester, phosphate, or phosphoramidite chemistry, by solid phase techniques such as described in EP 266,032, or by deoxynucleoside H-phosphonate intermediates. Enzymatically-produced nucleic acid can be made, for example, by amplification reactions, such as polymerase chain reaction (PCR) (see, e.g., U.S. Pat. Nos. 4,683,202 and 4,682,195, or by the synthesis of oligonucleotides described in U.S. Pat. No. 5,645,897. Biologically-produced nucleic acid include recombinant nucleic acid production in living cells, such as bacterial, yeast, and human cells. (See generally Sambrook and Russell, *Molecular Cloning, A Laboratory Manual* (3rd ed. 2001); Ausubel et al. (eds.), *Current Protocols in Molecular Biology* (1994); Sambrook et al., *Molecular Cloning, A Laboratory Manual* (2nd ed. 1989).)

The nucleic acid encoding the neurotoxic polypeptide can be, for example, an expression construct. Expression constructs encoding a neurotoxic polypeptide can be prepared by recombinant nucleic acid technology. An expression construct can include, for example, at least one nucleic acid encoding the neurotoxic polypeptide. In certain embodiments, an expression construct can include all or a portion of the DNA sequences identified by Database Accession numbers: Genbank NM_000345 for α-synuclein; Genbank NT_006081, for the accession number for chromosome 4 where the Huntingtin gene is located; Genbank AX460946 and AX460944, for the accession numbers for mutant forms of the Huntingtin gene; and Genbank NM_002111 for the mRNA sequence expressed by the Huntingtin gene.

A nucleic acid encoding a neurotoxic polypeptide can be combined with other nucleic acid sequences, including but not limited to, one or more promoters, enhancers, polyadenylation signals, restriction enzyme sites, multiple cloning sites, coding segments, and the like, to create one or more expression construct(s). The overall length can vary considerably between expression constructs. Thus, a nucleic acid segment of almost any length can be employed, with the total length preferably being limited by the ease of preparation or use in the intended recombinant nucleic acid protocol.

The expression of the neurotoxic polypeptide is typically directed by a promoter. A promoter can be naturally associated with a nucleic acid sequence, as can be obtained by isolating the 5' non-coding sequences located upstream of the coding segment and/or exon. Such a promoter can be referred to as "endogenous." Alternatively, the promoter can be "heterologous," from a different gene, or from a gene from a different species of organism. In some embodiments, expression of the neurotoxic polypeptide can be controlled by an inducible promoter, such as, for example, Gal1-10, Gal1, GalL, GalS, or CUP1 or a repressible promoter, such as Met25, for expression in yeast. (See generally Ausubel et al. (supra).) An expression construct can include at least one termination signal and/or polyadenylation signal, as needed.

Nucleic acids, such as expression constructs, can be introduced into cells of a eukaryotic cell expression system, such as a yeast cell, using a nucleic acid vector, including but not limited to, plasmids, linear nucleic acid molecules, artificial chromosomes and episomal vectors. Yeast plasmids, including integrating, centromere, autonomously replicating, and 2 micron vectors, are typically used for recombinant expression in yeast. Yeast plasmids typically include an antibiotic resistance gene, a bacterial origin of replication (for propagation in bacterial cells), and a selectable marker for maintenance in yeast cells. The yeast selectable marker is typically a nutritional gene (or "auxotrophic marker") such as, for example, TRP1, URA3, LEU2, HIS3 and/or LYS2.

Exemplary integrating vectors include YIp vectors, which are typically maintained in yeast by integration into the chromosomal DNA. Integrating vectors typically include a gene of interest (e.g., encoding the neurotoxic polypeptide), a bacterial origin of replication, and a selectable marker.

Exemplary centromere vectors include YCp and related plasmids, which typically contain an autonomous replicating sequence (e.g., ARS1), a centromere sequence (e.g., CEN4), a gene of interest (e.g., encoding the neurotoxic polypeptide), a bacterial origin of replication, and a selectable marker. Centromere plasmids are usually present at 1-2 copies per cell. Removal of the CEN sequence yields a replicative YRp plasmid, which is typically present in 100-200 copes per cell, and can be mitotically and meiotically unstable.

2 micron vectors contain a 2 micron sequence, which acts as a yeast replicon giving rise to higher plasmid copy number. The plasmid copy number can be increased by using a selectable marker operatively linked to a crippled promoter. This selectable marker is typically the LEU2 gene with a truncated promoter (LEU2-d), such that low levels of the Leu2p protein are produced. Examples of 2 micron vectors include YEp plasmids, such as YEp24 and the YEplac series of plasmids. (See, e.g., Sikorski, *Plasmid, A Practical Approach* (ed. K. G. Hardy), IRL Press (1993); and *Yeast Cloning Vectors and Genes, Current Protocols in Molecular Biology*, Section II, Unit 13.4, Eds., Ausubel et al. (1994).) pYES2 plasmids, available from Invitrogen (Carlsbad, Calif.), are also suitable.

An expression construct can also be introduced into a cell of a eukaryotic cell expression system by homologous recombination. Yeast and other organisms perform homologous recombination such that a free end of a nucleic acid can recombine with a homologous nucleic acid in the cell, which results in insertion of the introduced nucleic acid into the chromosomal DNA.

In certain embodiments, the expression of the neurotoxic polypeptide can be increased to increase toxicity. Levels of the neurotoxic polypeptide can be increased, for example, by expressing a nucleic acid encoding the neurotoxic polypeptide using a "strong" promoter and/or increasing the copy number of the nucleic acid encoding the neurotoxic polypeptide. For example, strong constitutive and inducible yeast promoters include the promoters for the genes encoding elongation factor 1 (TEF1 and TEF2), alcohol dehydrogenase I(ADHI) promoter, the GAL1-GAL10 promoter, the CUP1 promoter, or the like. The copy number of the nucleic acid encoding the neurotoxic polypeptide can be increased, for example, by including it in a high copy number plasmid, such as a Yep or YRp plasmid.

The nucleic acid encoding the neurotoxic polypeptide can be introduced into cells of a eukaryotic cell expression system according to methods known to the skilled artisan. For example, yeast cells are typically transformed by chemical methods, such as the lithium acetate method (e.g., as described by Rose et al., *Methods in Yeast Genetics*, Cold Spring Harbor Laboratory Press, Cold Spring Harbor, N.Y. (1990)). Transformed cells are then isolated on selective media. Yeast cells transformed with a nucleic acid can be identified, for example, by including a marker in the expression vector. Methods of introducing nucleic acids into other eukaryotic cells are known in the art. (See, e.g., Sambrook and Russell, supra; Ausubel et al., supra; Sambrook et al., supra.)

One or more homologs or orthologs of genes causing toxicity or enhanced toxicity of a neurotoxic polypeptide also can be expressed in the eukaryotic cell expression system using recombinant technology, as described herein or as known to the skilled artisan.

The eukaryotic cell expression systems are used to screen candidate agents to identify those agents that reduce or ameliorate toxicity of the neurotoxic polypeptide. Without intending to be bound by any particular theory, candidate agents can, for example, reduce or prevent protein misfolding, aggregation, accumulation, localization and/or deposition (e.g., in inclusion bodies). Irrespective of the exact mechanism of action, a candidate agent identified by the screening methods according to the present invention can provide a therapeutic benefit to patients with neurodegenerative disease, or can be used as a lead compound to develop a therapeutic agent. A "therapeutic benefit," in the context of the present invention, refers to any promotion or enhancement of the well-being of the subject with respect to the medical treatment of the subject's condition, which includes treatment of neurodegenerative disease, such as Huntington's and Parkinson's diseases. A nonexhaustive list of examples of therapeutic benefits includes extension of the subject's life by any period of time; decrease or delay in the development of the disease; decrease in number of protein aggregates, plaques, or fibrils; reduction in fibril growth; reduction in number of misfolded proteins; delay in onset of lapse in mental capabilities; and a decrease in atrophy or dementia to the subject that can be attributed to the subject's condition.

In certain embodiments, the screening methods according to the present invention utilize yeast expression systems that express the neurotoxic polypeptide. As discussed above, the cells of the first expression system have a genetic background in which the neurotoxic polypeptide is toxic. In the second expression system, cells are typically congenic to those of the first expression system, and the lack of the wild-type gene that enhances toxicity of the neurotoxic polypeptide yields cells in which this toxicity is suppressed relative to the first expression system. The toxic phenotype is typically manifested by growth inhibition, growth arrest, or cell death. For example, expression of the huntingtin fragment in a first yeast cell expressing a wild-type gene that enhances toxicity of the huntingtin fragment and having a suitable genetic background causes the yeast cell to be severely growth retarded or causes it to die when the huntingtin fragment is expressed. Contacting such a yeast cell with one or more ("at least one") candidate agent facilitates identification of one or more agents that can reduce the toxicity (also referred to as a "toxic phenotype"), such as by alleviating growth inhibition and/or cell death. If a second yeast cell (not expressing the wild-type gene) does not substantially exhibit alleviation of toxicity (relative to, e.g., a control cell (expressing the neurotoxic polypeptide but not the wild-type gene) not contacted with the agent), and/or the first cell contacted with the agent does not exhibit a reduction of toxicity relative to the second yeast cell contacted with the agent, the agent is identified as a potential therapeutic agent for the treatment of a disease associated with the neurotoxic polypeptide. Such an identified candidate agent may also reduce or prevent neurotoxicity of the neurotoxic polypeptide in humans (e.g., the accumulation of huntingtin protein in a human cell), thereby providing a method of identifying a potential therapeutic agent (or lead compound) for the development of a therapeutic agent for the treatment of humans having the neurodegenerative disease. Such a therapeutic agent may be used, for example, to prevent, treat and/or ameliorate the symptoms of Huntington's disease, Parkinson's disease, or the like.

A candidate agent can be contacted with the cell according to the characteristics of the candidate agent and the cell. A cell can be contacted with a nucleic acid by transformation. A cell also can be contacted with a candidate agent by culturing the cell in media containing the candidate agent. For example, a yeast cell can be contacted with a candidate agent by culturing the cell in liquid media, or growing the cell on solid or semi-solid media containing the candidate agent. In certain embodiments, the cell wall of a yeast cell can be partially removed to generate a spheroplast, and the spheroplast contacted with the candidate agent. The spheroplasts optionally can regenerate in the presence of the candidate agent. Similarly, insect and mammalian cells can be contacted with a candidate agent by including the agent in the culture media.

In an animal model system, the cell can be contacted with the candidate agent by administering the candidate agent to the animal. The candidate agent can be administered orally, intravenously, by infusion or injection, or the like.

Genetic agents can be screened by contacting the cell of the expression system with a nucleic acid encoding a gene or gene fragment. In a specific example, a genomic or cDNA library can be introduced into a yeast cell to identify a candidate agent that reduces the toxicity of the neurotoxic polypeptide. The library can be homologous or heterologous with respect to the cell expression system. For example, if the cell expression system is yeast, the library could from a non-yeast source, such as a human, mammalian, or bacterial source.

In certain embodiments, the library optionally can be prescreened or treated to reduce the number of copies of nucleic acids encoding the wild-type gene, or a homolog(s) thereof. Thus, in certain embodiments, a candidate agent is identified which is a nucleic acid, provided that the candidate agent is not a nucleic acid containing the wild-type gene, and/or provided that the candidate agent is not a nucleic acid containing a homolog of the wild-type gene.

In other examples, cells of the expression system can be contacted with proteinaceous candidate agents, such as proteins, polypeptides, and/or peptides. Suitable proteinaceous candidate agents that can be screened include homologous and heterologous proteins, including chaperones, hormones, growth factors, neurotransmitters, heat shock proteins, receptors, enzymes, ligands, regulatory factors, structural proteins, and proteinaceous drugs. Candidate agents also can include, for example, nuclear proteins, cytoplasmic proteins, mitochondrial proteins, secreted proteins, membrane-associated proteins, serum proteins, viral proteins, bacterial proteins, protozoal proteins, and/or parasitic proteins. Candidate agents can additionally include proteinaceous materials such as unmodified proteins, polypeptide and/or peptides as well as lipoproteins, glycoproteins, phosphoproteins, and nucleases.

In addition, cells of the expression system can be contacted with random and/or semi-random libraries of peptides and/or nucleic acids. In related embodiments, cells of the expression system can be contacted with peptidomimetics. The term "peptidomimetic" refers to a synthetic chemical compound that has substantially the same structural and functional characteristics as a protein, polypeptide, or peptide. Peptide analogs are commonly used in the pharmaceutical industry as non-peptide drugs with properties analogous to those of the template peptide. These types of non-peptide compounds are termed "peptide mimetics" or "peptidomimetics" (see, e.g., Fauchere, *J. Adv. Drug Res.* 15:29 (1986); Veber and Freidinger *TINS* p. 392 (1985); and Evans et al., *J. Med. Chem.* 30:1229 (1987)). Peptide mimetics that are structurally similar to therapeutically useful peptides may be used to produce an equivalent or enhanced therapeutic or prophylactic effect. Generally, peptidomimetics are structurally similar to a paradigm polypeptide (e.g., a polypeptide that has a desired biological or pharmacological activity), but have one or more peptide linkages optionally replaced by a linkage selected from the group consisting of, e.g., —$CH_2NH$—, —$CH_2S$—, —$CH_2$—$CH_2$—, —CH.=CH— (cis and trans), —$COCH_2$—, —CH(OH)$CH_2$—, and —$CH_2SO$—. The mimetic can be either entirely composed of synthetic, non-natural analogues of amino acids, or, is a chimeric molecule of partly natural peptide amino acids and partly non-natural analogs of amino acids. The mimetic can also incorporate natural amino acid conservative substitutions as long as such substitutions also do not substantially alter the mimetic's structure and/or activity.

Candidate agents also can be from libraries of synthetic and/or natural compounds. One example is a library of FDA-approved compounds that can be used by humans. In addition, synthetic compound libraries are commercially available from a number of companies including Maybridge Chemical Co. (Trevillet, Cornwall, UK), Comgenex (Princeton, N.J.), Brandon Associates (Merrimack, N.H.), and Microsource (New Milford, Conn.), and a rare chemical library is available from Aldrich (Milwaukee, Wis.).

Combinatorial libraries are available and/or can be prepared. Alternatively, libraries of natural compounds in the form of bacterial, fungal, plant, and animal extracts are also available, for example, from Pan Laboratories (Bothell, Wash.) or MycoSearch (N.C.), or can be prepared. Compounds isolated from natural sources, such as animals, bacteria, fungi, plant sources, including leaves and bark, and marine samples also can be screened as candidate agents.

Other suitable candidate agents include antisense molecules, ribozymes, and antibodies (including single chain antibodies and Fv fragments). For example, an antisense molecule that binds to a translational or transcriptional start site, or a splice junction, can be a candidate agent. Additionally, natural and synthetically-produced libraries and compounds are readily modified through conventional chemical, physical, and biochemical means.

Screening of such libraries, including combinatorially generated libraries (e.g., peptide libraries) can be performed in a rapid and efficient way to screen a large number of related and/or unrelated compounds. Combinatorial approaches also lend themselves to rapid evolution of potential therapeutic agents by the creation of second, third and fourth generation compounds modeled on active, but otherwise undesirable compounds.

Candidate agents can be found within compounds of numerous chemical classes, though typically they are organic compounds, and can include small organic compounds. Small organic compounds have a molecular weight of more than 50 yet less than about 2,500 daltons, typically less than about 750, or less than about 350 daltons. Exemplary classes include heterocycles, peptides, saccharides, steroids, triterpenoid compounds, or the like. Structural identification of an agent can be used to identify, generate, or screen additional candidate agents. For example, where peptide agents are identified, they can be modified in a variety of ways to enhance their stability, such as using an unnatural amino acid, such as a D-amino acid, by functionalizing the amino or carboxylic terminus (e.g., for the amino group, acylation or alkylation, and for the carboxyl group, esterification or amidification), or the like.

Preparation and screening of combinatorial chemical libraries is well known to those of skill in the art. Such combinatorial chemical libraries include, but are not limited to, peptide libraries (see, e.g., U.S. Pat. No. 5,010,175; Furka, *Int. J. Pept. Prot. Res.* 37:487-93 (1991); and Houghton et al., *Nature* 354:84-88 (1991)). Other chemistries for generating chemical diversity libraries also can be used. Such chemistries include, but are not limited to: peptoids (see, e.g., PCT Publication No. WO 91/19735), encoded peptides (see, e.g., PCT Publication WO 93/20242), random bio-oligomers (see, e.g., PCT Publication No. WO 92/00091), benzodiazepines (see, e.g., U.S. Pat. No. 5,288,514; and Baum, *C&EN*, Jan. 18, 1993, p. 33), diversomers such as hydantoins, benzodiazepines and dipeptides (see, e.g., Hobbs et al., *Proc. Nat. Acad. Sci. USA* 90:6909-13 (1993)), vinylogous polypeptides (see, e.g., Hagihara et al., *J. Amer. Chem. Soc.* 114:6568 (1992)), nonpeptidal peptidomimetics with glucose scaffolding (see, e.g., Hirschmann et al., *J. Amer. Chem. Soc.* 114:9217-18 (1992)), analogous organic syntheses of small compound libraries (see, e.g., Chen et al., *J. Amer. Chem. Soc.* 116:2661 (1994)), oligocarbamates (see, e.g., Cho et al., *Science* 261: 1303 (1993)), peptidyl phosphonates (see, e.g., Campbell et al., *J. Org. Chem.* 59:658 (1994)), nucleic acid libraries (see, e.g., Ausubel et al. (supra), and Sambrook, (supra)), peptide nucleic acid libraries (see, e.g., U.S. Pat. No. 5,539,083), antibody libraries (see, e.g., Vaughn et al., *Nature Biotechnology*, 14(3):309-14 (1996) and PCT/US96/10287), carbohydrate libraries (see, e.g., Liang et al., *Science* 274:1520-22 (1996) and U.S. Pat. No. 5,593,853), small organic molecule libraries, such as isoprenoids (see, e.g., U.S. Pat. No. 5,569, 588), thiazolidinones and metathiazanones (see, e.g., U.S. Pat. No. 5,549,974), pyrrolidines (see, e.g., U.S. Pat. Nos. 5,525,735 and 5,519,134), morpholino compounds (see, e.g., U.S. Pat. No. 5,506,337), or the like.

Devices for the preparation of combinatorial libraries are commercially available (see, e.g., 357 MPS, 390 MPS, Advanced Chem Tech, Louisville Ky.; Symphony, Rainin, Woburn, Mass.; 433A Applied Biosystems, Foster City, Calif.; 9050 Plus, Millipore, Bedford, Mass.). In addition, numerous combinatorial libraries are themselves commercially available (see, e.g., ComGenex, Princeton, N.J.; Tripos, Inc., St. Louis, Mo.; 3D Pharmaceuticals, Exton, Pa.; Martek Biosciences, Columbia, Md.; etc.).

Candidate agents that are initially identified by any of the foregoing screening methods can be further tested to validate the apparent activity. Typically, such studies are conducted by re-screening the agents. Alternatively, if a candidate agent is identified in one eukaryotic cell expression system (e.g., a yeast expression system), the identified candidate agent can be further characterized in another model system, such as a rat, mouse, *Drosophila* or *C. elegans* system, or cells isolated from such an organism or ex vivo human cells. Subsequent validation also can be performed with suitable animal models. The basic format of such methods can involve administering a lead compound identified during an initial screen to an animal that serves as a model for the human neurodegenerative disease and then determining if neurotoxicity is modulated. The animal models utilized in validation studies generally are mammals of any kind. Specific examples of suitable animals include, but are not limited to, primates, mice and rats.

B. Biological Activities of Proteins Enhancing Neurotoxic Polypeptides and Related Methods In another aspect, methods are provided for screening candidate agents based on a biological activity associated with a wild-type protein that enhances toxicity of a neurotoxic polypeptide. The methods generally include the following steps: (1) contacting with a candidate agent a sample of a wild-type protein that enhances toxicity of a neurotoxic polypeptide when expressed in a cell; (2) determining the level of a biological activity associated with the protein relative to a control sample of protein that has not been contacted with the candidate agent; and (3) if the sample of protein contacted with the agent exhibits a substantial decrease in the biological activity relative to the control sample, then (a) contacting a eukaryotic cell expressing the wild-type protein and the neurotoxic polypeptide, wherein expression of the neurotoxic polypeptide is toxic to the cell; and (b) determining for the cell the level of a biological activity associated with the toxicity of the neurotoxic polypeptide, said level relative to a control eukaryotic cell that expresses the wild-type protein and the neurotoxic polypeptide and that has not been contacted with the candidate agent, whereby if the cell contacted with the agent exhibits a substantial decrease in the biological activity relative to the control cell, the agent is identified as a potential therapeutic agent for the treatment of a disease associated with the neurotoxic polypeptide.

The method optionally includes contacting a second eukaryotic cell with the candidate agent, where the second cell expresses the neurotoxic polypeptide and does not express the wild-type protein, and determining for the second cell the level of the biological activity associated with expression of the neurotoxic polypeptide. The agent is identified as a potential therapeutic for the treatment of a disease associated with the neurotoxic polypeptide if the first cell, expressing the neurotoxic polypeptide and wild-type protein and contacted with the agent, exhibits a substantial decrease of the biological activity relative to the control cell that has not been contacted with the agent, but does not exhibit a substantial decrease of the biological activity relative to the second eukaryotic cell.

In certain embodiments, the neurotoxic polypeptide is a huntingtin polypeptide comprising an expanded polyQ repeat, and the wild-type protein is BNA4, CYK3, DEF1, ECM37, MBF1, MGT1, MSO1, PAF1, RDH54, RXT3, SNA2, KEX1, VPS53, YBR016W, YDR287W, YER185W, YLR278C, YMR082C, HSP104, NHP6B, SMY2, YLR454W, PHO87, RNQ1, BFR1, MSL1, UME-1, YIR003W, YMR244C-A, ARG7, YCL005W, BNA1, VPS60, YBR241C, YDR459C, YMR075C-A, YMR086W, COX5B, NUP2, or YDJ1. Particularly suitable wild-type proteins include BNA4, CYK3, DEF1, ECM37, MBF1, MGT1, MSO1, PAF1, RDH54, RXT3, SNA2, VPS53, YBR016W, YDR287W, YER185W, YLR278C, YMR082C, NHP6B, SMY2, YLR454W, PHO87, RNQ1, BFR1, UME-1, YIR003W, YMR244C-A, and ARG7. In certain preferred variations, the wild-type protein is BNA4, CYK3, DEF1, MBF1, MGT1, PAF1, RDH54, VPS53, YBR016W, YDR287W, NHP6B, SMY2, YLR454W, PHO87, RNQ1, UME-1, or YMR244C-A, more preferably BNA4, CYK3, MBF1, MGT1, YDR287W, or PHO87. In some variations, the wild-type protein is not DEF1, YBR016W, RNQ1, or YIR003W.

In other embodiments in which the neurotoxic polypeptide is a huntingtin polypeptide, the wild-type protein is BNA4, DEF1, MBF1, MSO1, PAF1, RDH54, SNA2, KEX1, YBR016W, YDR287W, YLR278C, YMR082C, NHP6B, YLR454W, MSL1, YIR003W, YMR244C-A, YMR086W, and NUP2. BNA4, DEF1, MBF1, PAF1, RDH54, KEX1, YBR016W, YDR287W, NHP6B, YLR454W, MSL1, YIR003W, YMR086W, and NUP2 are particularly suitable.

In further variations in which the neurotoxic polypeptide is a huntingtin polypeptided, the wild-type protein is KMO, SH3GL2, FLJ39117, TXNDC2, EDF1, MGMT, PD2, RAD54B, PPGB, FLJ10979, SS18, IMPA1, SKD, HMGB2, PERQ1, KIAA0100, SLC13A5, SNRPA, NUP43, TXNDC2, HAAO, SLC2A1, ZDHHC15, SEMG2, RANBP2, or DNAJA2. Particularly suitable wild-type proteins include KMO, SH3GL2, FLJ39117, TXNDC2, EDF1, MGMT, PD2, RAD54B, FLJ10979, SS18, IMPA1, HMGB2, PERQ1, KIAA0100, SLC13A5, and NUP43. For example, in one preferred embodiment, the wild-type protein is KMO, SH3GL2, EDF1, MGMT, IMPA1, or SLC13A5. In certain varations, the wild-type protein is not FLJ39117, TXNDC2, or SS18. In other embodiments, the wild-type protein is KMO, TXNDC2, EDF1, PD2, RAD54B, PPGB, SS18, IMPA1, HMGB2, KIAA0100, SNRPA, SEMG2, or RANBP2.

In other embodiments, the neurotoxic polypeptide is an α-synuclein polypeptide and the wild-type protein is VTS1, LPH17, YIM1, UBP2, VAM3, BUL1, SAL6, YOR138C, VPS30, RAV1, VPS38, SCP160, KAR5, YJR111C, YAP3, HAL9, YHL044W, YKL077W, LHS1, YPK1, UBP12, VPS13, YCL005W, YHM1, PUF4, YER030W, YBL083C, GIM4, YCL075W, MRPL13, HDA1, YBR027C, APT2, PMD1, GIM5, DHH1, BUD31, SFL1, FIG4, HSL1, PPG1, YCK2, SSK22, SPL2, PKH1, KNS1, SYT1, YPT53, YPS1, YPS3, DOA1, BRE5, YDR119W, YBT1, PDR5, or PDR16. Particularly suitable wild-type proteins include VTS1, UBP2, VAM3, VPS38, SCP160, YAP3, HAL9, YKL077W, YPK1, YBL083C, MRPL13, APT2, FIG4, and DOA1. In a preferred variation, the wild-type protein is VTS1, UBP2, VAM3, SCP160, or YPK1.

In other embodiments in which the neurotoxic polypeptide is an α-synuclein polypeptide, the wild-type protein is VTS1, LPH17, YIM1, UBP2, VAM3, BUL1, SAL6, YOR138C, VPS30, RAV1, VPS38, SCP160, KAR5, YJR111C, YAP3, HAL9, YHL044W, YKL077W, LHS1, YPK1, UBP12, VPS13, YCL005W, YHM1, PUF4, YER030W, YBL083C, GIM4, YCL075W, MRPL13, HDA1, YBR027C, APT2, PMD1, GIM5, DHH1, BUD31, or SFL1. VTS1, LPH17, YIM1, UBP2, VAM3, SAL6, VPS30, RAV1, SCP160, LHS1, YPK1, UBP12, VPS13, YHM1, PUF4, GIM4, HDA1, APT2, PMD1, GIM5, DHH1, BUD31, and SFL1 are particularly suitable.

In further variations in which the neurotoxic polypeptide is an α-synuclein polypeptide, the wild-type protein is FLJ10211, ADCK2, RTN4IP1, USP28, STX16, PPP1CB, BECN1, DMXL1, RC3, HDLBP, HYOU1, SGK2, USP15, VPS13A, SLC25A15, PUM2, PFDN2, HDAC6, APRT, DSPP, PFDN5, DDX6, G10, HSF4, SAC3, STK29, KIAA1811, PPP4C, CSNK1G2, MAP3K4, MAP3K5, PDPK1, CLK1, BIG1, RAB5C, RAB5A, PGC, PLAA, G3BP2, ABCC1, ABCG2, or PTPN9. Particularly suitable wild-type proteins include FLJ10211, USP28, STX16, STX1B2, HDLBP, and SGK2. In other embodiments, the wild-type protein is FLJ10211, ADCK2, RTN4IP1, USP28, STX16, PPP1CB, BECN1, DMXL1, RC3, HDLBP, HYOU1, SGK2, USP15, VPS13A, SLC25A15, PUM2, PFDN2, HDAC6, APRT, DSPP, PFDN5, DDX6, G10, or HSF4.

1. Assays for Biological Activity of Wild-Type Protein

The wild-type protein that enhances toxicity of the neurotoxic polypeptide is assayed for any biological activity associated with a normal function of the protein. Tables 3-5, infra, list some examples of functions and associated biological activities of the wild-type proteins set forth above.

TABLE 3

| | Exemplary functions, associated biological activities, and/or biochemical characteristics of yeast proteins enhancing polyQ toxicity | |
|---|---|---|
| Protein | Associated Cellular Activity | Function/Associated Biological Activity/Biochemical Characteristic(s) |
| BNA4 | NADH metabolism | Kynurenine 3-hydroxylase, NADPH-dependent flavin monooxygenase that catalyzes the hydroxylation of kynurenine to 3-hydroxykynurenine in tryptophan degradation and nicotinic acid synthesis; interacts with GCS1 (which activates Arf1 and Arf2) |
| CYK3 | cytokinesis | Protein involved in cytokinesis; defective in targeting Prc1; in a complex with bnr1; human ortholog involved in synaptic vesicle fission |
| DEF1 | Meiosis; Ubiquitin-dependent protein catabolism | Protein involved in vacuolar import and degradation, glutamine rich; required for DNA damage-induced degradation of RNA polymerase II: VID 31; contains Q/N-rich regions which may mediate prion-like aggregation |
| ECM37 | cell wall organization and biogenesis | Protein possibly involved in cell wall structure or biosynthesis |
| MBF1 | transcription from Pol II promoter | Transcriptional coactivator of Gcn4p |
| MGT1 | Mitochondrial genome maintenance; DNA repair | O6-methylguanine DNA repair methyltransferase that carries out a suicide reaction |
| MSO1 | post-golgi transport | Putative component of secretory vesicle docking complex, functions in association with Sec1p |
| PAF1 | transcription initiation from a Pol II promoter | Protein associated with RNA polymerase II, involved in positive and negative regulation, may be involved in transcription elongation; |
| RDH54 | G2/M transition of mitotic cell cycle; Meiotic recombination | Protein required for mitotic diploid-specific recombination and repair and for meiosis |
| SNA2 | protein-vacuolar targeting | Protein involved in Prc1p, Pep4p, and Pho8p trafficking to the vacuole |
| KEX1 | toxic metabolism | Carboxypeptidase specific for C-terminal Arg or Lys, involved in processing precursors of alpha-factor and K1 and K2 killer toxins |
| VPS53 | vesicle-mediated transport | Subunit of the VFT (Sac2p-Vps53p-Luv1p) complex, involved in protein sorting in the late Golgi |
| YBR016W | | Plasma membrane protein containing a Q/N-rich domain which may mediate prion-like aggregation |
| YDR287W | signal transduction; phospholipid metabolism | Inositol monophosphatase, catalyzes hydrolysis of inositol-1-phosphate, involved in the inositol cycle of calcium signaling |
| YER185W | response to toxin | Member of the RTA1-like protein family, which may be involved with response to toxin, has a region of weak similarity to a region of *S. cerevisiae* Rsb1p, which is involved in the release of sphingoid long-chain bases from the cytoplasm to the medium |
| YLR278C | transcription from Pol II promoter | Contains Q/N-rich regions which may mediate prion-like aggregation; Protein with similarity to transcription factors, contains an N-terminal Zn[2]-Cys[6] fungal-type binuclear cluster domain; transcription from Pol II promoter |
| HSP104 | Response to oxidative stress; protein folding | Heat shock protein required for induced thermotolerance and for resolubilizing aggregates of denatured proteins, important for the [psi−] to [PSI+] prion conversion, may be required for ethanol and acetaldehyde resistance |
| NHP6B | Transcription from Pol III promoter; Protein complex assembly | Protein with DNA-binding and DNA-bending activity, involved in transcriptional activation of a number of genes, functionally redundant with Nhp6Ap |
| SMY2 | | Suppresses myo2-66, sec22, bet1, sec16-3, spt15, and yrb1-51 mutants when overexpressed |

TABLE 3-continued Exemplary functions, associated biological activities, and/or biochemical characteristics of yeast proteins enhancing polyQ toxicity

| Protein | Associated Cellular Activity | Function/Associated Biological Activity/Biochemical Characteristic(s) |
| --- | --- | --- |
| PHO87 | Phosphate metabolism; transport; Phosphate transport | Member of the phosphate permease family of membrane transporters, appears to play a supporting role in phosphate uptake under high phosphate growth conditions |
| RNQ1 | Response to drug | Protein required for resistance to certain drugs, association with Sis1p leads to formation of [RNQ+] prion |
| BFR1 | mRNA metabolism | Protein that suppresses brefeldin A-induced lethality when overproduced, may be involved in mRNA metabolism; defects in targeting Prc1 |
| MSL1 | response to stress | U2 snRNA-associated protein with similarity to U2B" protein, has one RNA recognition (RRM) domain; response to stress; null has defects in targeting Prc1 to the vacuole |
| UME-1 | meiosis | Negative regulator of meiosis, represses meiotic gene expression in mitotically-growing cells, interacts with Rpd3p and Sin3p; negative regulation of transcription from Pol II promoter |
| YIR003W | | Protein that interacts with Abp1p (nonselective vesicle transport) through a C-terminal SH3 binding motif, has similarity to *E. coli* and *Bacillus subtilis* MinD |
| YMR244C-A | | Protein having moderate similarity to uncharacterized *C. albicans* Ipf660p |
| ARG7 | Ornithine metabolism; Amino acid biosynthesis | Ornithine acetyltransferase, catalyzes the fifth step in ornithine and arginine biosynthesis, also has acetylglutamate synthase activity |
| BNA1 | NADH metabolism | 3-hydroxyanthranilate 3,4-dioxygenase, involved in biosynthesis of nicotinic acid from tryptophan |
| VPS60 | vesicle-mediated transport | Protein with possible role in vacuolar protein sorting, has similarity to Snf7p, mutant exhibits characteristics of class E vps mutants |
| YBR241C | Organelle organization and biogenesis | Protein with high similarity to *S. cerevisiae* Vps73p, which is a putative hexose transporter and class B vacuolar sorting protein involved in *S. cerevisiae* Prc1p vacuolar trafficking pathway, member of the sugar (and other) transporter family |
| YDR459C | | Member of the DHHC zinc finger domain containing family, which may be involved in protein-protein or protein-DNA interactions, has weak similarity to uncharacterized mouse 6030457O13Rik |
| YMR086W | | in complex with Arf1 and Snf1 |
| COX5B | Transport; Aerobic respiration | Cytochrome c oxidase chain Vb, expressed under anaerobic conditions |
| NUP2 | Nucleocyto-plasmic transport; Loss of chromatin silencing; Protein-nucleus export | Nuclear pore protein (nucleoporin) with XFXFG motifs; has functional overlap with other proteins of nuclear pore complex; member of a family of natively unfolded proteins; human homologue is a SUMO ligase |
| YDJ1 | Protein-mitochondrial targeting [E]; Binding unfolded ER proteins [E]; Response to stress | Protein involved in protein import into mitochondria and ER, homolog of *E. coli* DnaJ |

TABLE 4

Exemplary functions, associated biological activities, and or biochemical characteristics of yeast proteins enhancing α-synuclein toxicity

| Protein | Function/Associated Biological Activity/Biochemical Characteristic(s) |
| --- | --- |
| VTS1 | RNA-binding protein that destabilizes SRE (Smg recognition element)-containing transcripts, confers allele-specific suppression of a vti1-2 mutation upon overproduction |
| LPH17 | Member of the ABC1 family, has high similarity to uncharacterized *C. albicans* Ipf1031p |
| YIM1 | Mitochondrial inner membrane protease, has sequence similarity to *E. coli* leader peptidase |

TABLE 4-continued

Exemplary functions, associated biological activities, and or biochemical characteristics of yeast proteins enhancing α-synuclein toxicity

| Protein | Function/Associated Biological Activity/Biochemical Characteristic(s) |
|---|---|
| UBP2 | Ubiquitin-specific protease (ubiquitin C-terminal hydrolase), cleaves at the C terminus of ubiquitin |
| VAM3 | Syntaxin homolog (t-SNARE), required for vacuolar assembly |
| BUL1 | Protein involved in the ubiquitination pathway |
| SAL6 | Protein serine/threonine phosphatase involved in regulation of protein synthesis, member of the PPP family of protein phosphatases and related to PP1 phosphatases |
| YOR138C | Protein containing a UBA (ubiquitin associated) or TS-N domain |
| VPS30 | Protein involved in sorting and delivery of soluble hydrolases to the vacuole, required for autophagy |
| RAV1 | Regulator of the (H+)-ATPase of vacuolar and endosomal membranes |
| VPS38 | Protein involved in vacuolar sorting |
| SCP160 | Protein involved in control of mitotic chromosome transmission, acts as an effector for Gpa1p in the mating response pathway, contains 14 KH domains which are found in RNA-binding proteins such as Mer1p and mouse hnRNP X |
| KAR5 | Coiled-coil membrane protein required for homotypic nuclear fusion |
| YJR111C | Member of the bacterial carboxymuconolactone decarboxylase family, which are involved in protocatechuate catabolism, has moderate similarity to uncharacterized *C. albicans* Ipf4704p |
| YAP3 | Transcription factor of the basic leucine zipper (bZIP) family, one of eight members of a novel fungal-specific family of bZIP proteins |
| HAL9 | Protein involved in salt tolerance, has similarity to transcription factors, contains a Zn[2]-Cys[6] fungal-type binuclear cluster domain in the N-terminal region |
| YHL044W | Member of the duplication (DUP) family, has low similarity to uncharacterized *S. cerevisiae* Ycr007p |
| YKL077W | Protein having moderate similarity to uncharacterized *C. albicans* Ipf15116p |
| LHS1 | Member of the Hsp70 superfamily required for efficient translocation of protein precursors across the ER membrane |
| YPK1 | Serine/threonine protein kinase involved in the cell integrity signaling pathway and required for endocytosis, possibly involved in a sphingolipid-mediated signaling pathway, has similarity to protein kinase C |
| UBP12 | Ubiquitin-specific protease, ubiquitin C-terminal hydrolase |
| VPS13 | Protein involved in vacuolar sorting |
| YHM1 | Protein involved in mitochondrial iron homeostasis, member of the mitochondrial carrier (MCF) family of membrane transporters, overproduction suppresses loss of Abf2p |
| PUF4 | Protein with pumilio repeats that is involved with Mpt5p in relocalization of Sir3p and Sir4p from telomeres to the nucleolus |
| GIM4 | Prefoldin subunit 2, component of the Gim protein complex that promotes formation of functional α- and γ-tubulin, and actin |
| YCL075W | Transposon TY5-1 16.0 kD hypothetical protein |
| MRPL13 | Mitochondrial ribosomal protein of the large subunit |
| HDA1 | Histone deacetylase, catalyzes removal of acetyl groups from histones, required for repression of many genes |
| APT2 | Adenine phosphoribosyltransferase (APRT), may be a heterodimer with Apt1p |
| PMD1 | Protein involved in negative regulation of early meiotic gene expression |
| GIM5 | Prefoldin subunit 5, component of the Gim protein complex that promotes formation of functional α-tubulin, γ-tubulin, and actin |
| DHH1 | Putative RNA helicase required for normal sporulation, member of the DEAD/DEAH-box RNA helicase family |
| BUD31 | Protein that may be involved in polar bud site selection in diploids, has similarity to *Xenopus* G10, a developmentally-regulated protein that is thought to be involved in translation during oocyte maturation |
| SFL1 | Transcriptional repressor interacting with SRB mediator subcomplex of RNA polymerase II, contains a putative heat shock factor (HSF) DNA-binding domain |
| FIG4 | $Mg^{2+}$ dependent PI(3,5)P2 phosphoinositide 5-phosphatase that putatively functions with Inp52p and Inp53p to regulate phosphatidylinositol 3,5 phosphate turnover, involved in regulating vacuole size |
| HSL1 | Serine/threonine protein kinase that genetically interacts with histone mutants and negatively regulates Swe1p protein kinase |
| PPG1 | Protein serine/threonine phosphatase involved in glycogen accumulation, member of the PPP family of protein phosphatases and related to PP2A phosphatases |
| YCK2 | Casein kinase I isoform |
| SSK22 | MAP kinase kinase kinase (MAPKKK) with strong similarity to Ssk2p, participates in the high-osmolarity signal transduction pathway |
| SPL2 | Putative inhibitor of Pho80p-Pho80p cyclin-dependent protein kinase, may block phosphorylation of other factors other than Pho4p |
| PHK1 | Serine/threonine protein kinase, functions similarly to mammalian 3-phosphoinositide-dependent protein kinase, phosphorylates and activates Ypk1p, required for endocytosis |
| KNS1 | Serine/threonine protein kinase involved in the cell integrity signaling pathway and required for endocytosis, possibly involved in a sphingolipid-mediated signaling pathway, has similarity to protein kinase C |

TABLE 4-continued

Exemplary functions, associated biological activities, and or biochemical characteristics of yeast proteins enhancing α-synuclein toxicity

| Protein | Function/Associated Biological Activity/Biochemical Characteristic(s) |
|---|---|
| SYT1 | Guanine nucleotide exhange factor, contains a conserved Sec7p-domain |
| YPT53 | GTP-binding protein involved in endocytosis and transport of proteins to the vacuole, member of the rab family in the ras superfamily |
| YPS1 | Yapsin 1, GPI-anchored aspartyl protease that cleaves C-terminal to paired basic residues (Aspergillopepsin I) |
| YPS3 | GPI-anchored aspartyl protease |
| DOA1 | Protein required in ubiquitin proteolysis and found complexed with Cdc48p, has WD (WD-40) repeats |
| BRE5 | Ubiquitin protease, associates with Ubp3p to de-ubiquitinate Sec23p, mutant is sensitive to brefeldin A |
| YDR119W | Member of the 14-spanner drug: [$H^+$] antiporter (DHA14) family of multidrug-resistance (MSF-MDR) proteins in the major facilitator superfamily (MFS) |
| YBT1 | Protein with similarity to mammalian ATP-dependent bile acid transporter, member of the ATP-binding cassette (ABC) superfamily |
| PDR5 | Drug efflux pump involved in the resistance to multiple drugs, member of the ATP-binding cassette (ABC) superfamily; inhibited by FK506 |
| PDR16 | Phosphatidylinositol transfer protein, involved in regulation of phospholipase D (Spo14p) activity, involved in lipid biosynthesis and multidrug resistance |

TABLE 5

Exemplary functions, associated biological activities, and/or biochemical characteristics of human orthologs of yeast proteins enhancing α-synuclein toxicity

| Protein | Function/Associated Biological Activity/Biochemical Characteristic(s) |
|---|---|
| FLJ10211 | Protein containing a SAM (sterile alpha motif) domain, which may mediate protein-protein interactions |
| ADCK2 | Member of the ABC1 family, has high similarity to uncharacterized mouse Adck2 |
| RTN4IP1 | NOGO-interacting mitochondrial protein, a mitochondrial protein that interacts with NOGO (RTN4) and with the mitochondrial complex III proteins UQCRC2 and UQCRC1, contains a zinc-binding alcohol dehydrogenase domain |
| USP28 | Protein with high similarity to ubiquitin specific protease 25 (human USP25), which is a C-terminal ubiquitin hydrolase, member of the ubiquitin carboxyl-terminal hydrolase family, which are cysteine proteases involved in deubiquitination |
| STX16 | Syntaxin 16, a t-SNAP receptor that interacts with STX6 and VTI1A possibly forming a specific t-SNARE complex, involved in the transport of early recycling endosomes to trans-Golgi network, may have a role in vesicle transport |
| STX1B2 | Protein with very strong similarity to syntaxin 2 (rat Stx1b2), which is involved in the docking and fusion of synaptic vesicles to the presynaptic plasma membrane in neural cells, member of the SNARE domain containing family, contains a syntaxin domain |
| PPP1CB | Protein phosphatase 1 catalytic subunit beta, catalytic subunit of a serine-threonine phosphatase, function in metabolic processes is modulated by regulatory subunits; differentially expressed in gastric cancer and neurons of Alzheimer Disease patients |
| BECN1 | Beclin, a BCL2 interacting cellular protein that protects cells from viral-induced apoptosis and may play a role in antiviral host defense; may also promote autophagy and inhibit cellular proliferation; possible tumor suppressor |
| DMXL1 | Dmx-like 1, a member of the WD repeat superfamily of proteins, contains at least 28 WD repeat units |
| RC3 | Rabconnectin-3, protein containing twelve WD domains (WD-40 repeats), predicted to associate with RAB3-GEP and RAB3GAP at synaptic vesicles |
| HDLBP | High density lipoprotein binding protein, binds and inhibits cleavage of the 3' UTR of vitellogenin mRNA, binds and promotes nuclear export of tRNA, binds high density lipoproteins and may have roles in cholesterol metabolism and atherogenesis |
| HYOU1 | Oxygen regulated protein 150 kDa, part of a large multichaperone-containing complex, a putative endoplasmic reticulum chaperone for angiogenic factors, induced in response to hypoxia, may be a useful marker of vascular pathology |
| SGK2 | Serum-glucocorticoid regulated kinase 2, a serine-threonine kinase that may be regulated by 3-phosphoinositide-dependent kinase-1 (PDK1) and by hydrogen peroxide |
| USP15 | Ubiquitin-specific protease 15, a member of the ubiquitin-specific cysteine (thiol) protease family, cleaves ubiquitin from ubiquitin-conjugated protein substrates, may play a role in growth regulation |
| VPS13A | Vacuolar protein sorting 13A, may be involved in protein sorting; mutation of the corresponding gene is associated with chorea acanthocytosis syndrome |

TABLE 5-continued

Exemplary functions, associated biological activities, and/or biochemical characteristics of human orthologs of yeast proteins enhancing α-synuclein toxicity

| Protein | Function/Associated Biological Activity/Biochemical Characteristic(s) |
|---|---|
| SLC25A | Solute carrier family 25 member 15 (mitochondrial ornithine transporter 1), an ornithine transporter that may play a role in the urea cycle; mutations in the gene cause hyperornithinemia-hyperammonemia-homocitrullinuria (HHH) syndrome |
| PUM2 | Pumilio (*Drosophila*) homolog 2, an RNA binding protein expressed primarily in spermatocytes and oocytes that interacts with DAZ and DAZL, may mediate translational repression in germ cell development |
| PFDN2 | Protein with strong similarity to prefoldin (mouse Pfdn2), which is a chaperone that delivers unfolded proteins to cytosolic chaperonin, member of the KE2 gene product family |
| HDAC6 | Histone deacetylase 6, member of the class II family of histone deacetylases, contains two catalytic domains that may function independently, may be involved in the repression of transcription and cell cycle control |
| APRT | Adenine phosphoribosyltransferase, an adenine salvage enzyme, may mediate sensitivity to the immunosuppressive drug mizoribine; deficiency leads to 2,8-dihydroxyadenine (DHA) urolithiasis that may result in renal failure |
| DSPP | Dentin sialophosphoprotein, a putative extracellular matrix protein that may play a role in dentin mineralization and tooth development; mutation of the corresponding gene is associated with dentinogenesis imperfecta Shields type II |
| PFDN5 | Prefoldin 5, a component of the prefoldin chaperone complex involved in delivery of unfolded proteins to cytosolic chaperonin, interacts with and may repress activation of MYC; candidate tumor suppressor commonly substituted in cancer cells |
| DDX6 | DEAD box protein 6, a member of the DEAD/H box ATP-dependent RNA helicase protein family, may be involved in cell proliferation, upregulated in colorectal adenocarcinoma and colonic adenoma; gene is translocated in a diffuse large B-cell lymphoma |
| G10 | Maternal G10 transcript, homolog of *Xenopus* G10, contains an N-terminal acidic domain and a cysteine-rich C-terminal domain with a putative zinc-finger motif, may be involved in nuclear regulation of transcription, induced by phorbol myristic acetate |
| HSF4 | Heat shock transcription factor 4, a tissue-specific transcription factor comprised of two alternative forms that exhibit opposing actions on heat shock gene expression; genetic mutations are associated with autosomal dominant lamellar and Marner cataract |
| SAC3 | Member of the SacI homology domain containing family, has moderate similarity to *S. cerevisiae* Fig4p, which is a lipid phosphatase that may function with *S. cerevisiae* Inp52p and *S. cerevisiae* Inp53p to regulate phosphatidylinositol 3,5 phosphate turnover |
| STK29 | Protein with high similarity to KIAA1811 protein (human KIAA1811), which is a protein kinase, contains a protein kinase domain |
| KIAA1811 | Protein kinase, activated by STK11-mediated phosphorylation, preferentially phosphorylates the LNR peptide, yet can also phosphorylate AMARA and SAMS peptides, expressed in neuronal tissues, member of the AMPK-related kinase family |
| PPP4C | Protein phosphatase 4 catalytic subunit, interacts with NF-KB and c-Rel (REL) and is involved in TNF-α (TNF) and JNK signaling pathways and microtubule organization at centrosomes |
| CSNK1G2 | Casein kinase 1 γ 2, a putative serine/threonine protein kinase, may play a role in signal transduction |
| MAP3K4 | Mitogen-activated protein kinase kinase kinase 4, phosphorylates MAP2K3, MAP2K6, and MAP2K4, induces MAPK14 and MAPK8 activation, mediates stress activation and cancer cell apoptosis involving MAPK14, BRCA1, and GADD45G |
| MAP3K5 | Mitogen activated protein kinase kinase kinase 5, activates SAPK, Jun kinase and p38 signaling pathways, acts in stress and cytokine-induced apoptosis, involved in cellular differentiation, may play a role in HIV and neurodegenerative disease |
| PDPK11 | 3-phosphoinositide-dependent protein kinase-1, has a pleckstrin homology domain, phosphorylates AKT1, p70s6k, PRKCD, PRKCZ, p21 activated kinase (PAK1), and mediates insulin-induced actin reorganization, activity is inhibited by celecoxib |
| CLK1 | A member of the LAMMER family of dual specificity protein kinases, a protein serine-threonine kinase that may play a role in cell cycle control and cell proliferation |
| BIG1 | Guanine nucleotide-exchange protein, sensitive to brefeldin A and may have a role in vesicular transport |
| RAB5C | RAB5C member RAS oncogene family (Ras-related GTP-binding protein 5C), putative GTPase involved in endosome to lysosome transport, absent from phagosomes containing virulent *Legionella pneumophila* and may contribute to their failure to fuse with lysosomes |
| RAB5A | RAB5 Ras-related GTP-binding protein 5, regulates endocytic transport and synaptic vesicle fusion, may contribute to cytotoxicity resulting from Lewy body formation in neurodegenerative disease through endocytosis of alpha-synuclein (SNCA) |

TABLE 5-continued

Exemplary functions, associated biological activities, and/or biochemical
characteristics of human orthologs of yeast proteins enhancing α-synuclein toxicity

| Protein | Function/Associated Biological Activity/Biochemical Characteristic(s) |
|---|---|
| PGC | Pepsinogen C (progastricsin), the inactive precursor of pepsin C (gastricsin), member of a family of aspartic proteinases, expression may be induced in some breast tumors; genetic variant is associated with an increased risk of gastric body ulcer |
| PLAA | Phospholipase A2 activating protein, may regulate phospholipase A2 activity, likely an important regulator of the production of eicosanoids and prostaglandin E(2) in an immune or inflammatory response; may be a tumor suppressor |
| G3BP2 | Ras-GTPase activating protein SH3 domain-binding protein 2, putative RNA binding protein that possesses ATPase activity, is phosphorylated and activated by heregulin (NRG1) and overexpressed in breast tumors that also overexpress HER2 (ERBB2) |
| ABCC1 | GS-X ATP-binding cassette subfamily C member 1 (multiple drug resistance protein 1), an ATP-binding cassette transporter that acts as a multidrug efflux pump conferring resistance to lipophilic drugs and chemotherapeutic agents |
| ABCG2 | MRX ATP-binding cassette subfamily G member 2 (breast cancer resistance protein), a drug transporting ATPase, transports sulfated steroids, implicated in multidrug resistance in cancer and resistance to reverse transcriptase inhibitors used to treat HIV |
| PTPN9 | Protein tyrosine phosphatase non-receptor type 9, activated by phosphatidylinositols binding, modulated by neutrophil phagocytosis, may play a role in regulation of phagocytosis and secretory vesicle formation; gene deletion may be associated with autism |

In certain embodiments, the wild-type protein is assayed in vitro for the biological activity. The wild-type protein, endogenously or recombinantly expressed in cells, can be isolated and purified by standard methods including chromatography (e.g., ion exchange, affinity, sizing column chromatography, high pressure liquid chromatography), centrifugation, differential solubility, or by any other standard technique for the purification of proteins. Alternatively, the protein can be synthesized by standard chemical methods known in the art (see, e.g., Hunkapiller et al., Nature 310:105-11 (1984); Stewart and Young, Solid Phase Peptide Synthesis, 2nd Ed., Pierce Chemical Co., Rockford, Ill., (1984)). The functional properties of the isolated or synthesized protein can be evaluated using any suitable assay as described herein or otherwise known to the skilled artisan.

In addition, fragments, derivatives, and analogs of wild-type polypeptides can be used for in vitro assays. For example, a peptide corresponding to a portion, or fragment, of a wild-type polypeptide that comprises a desired domain and mediates a desired activity in vitro can be synthesized by use of chemical synthetic methods using, for example, an automated peptide synthesizer.

Furthermore, if desired, nonclassical amino acids or chemical amino acid analogs can be introduced as a substitution or addition into the wild-type polypeptide sequence. Non-classical amino acids include but are not limited to the D-isomers of the common amino acids, α-amino isobutyric acid, 4-aminobutyric acid, 2-amino butyric acid, γ-amino butyric acid, ε-Ahx, 6-amino hexanoic acid, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, β-alanine, selenocysteine, fluoro-amino acids, designer amino acids such as β-methyl amino acids, C α-methyl amino acids, N α-methyl amino acids, and amino acid analogs in general. Furthermore, the amino acid can be D (dextrorotary) or L (levorotary).

In certain embodiments, the wild-type protein, or fragment or derivative thereof, is a chimeric, or fusion, protein comprising the polypeptide or fragment thereof (typically consisting of at least a domain or motif of the wild-type polypeptide, or at least 10 contiguous amino acids of the wild-type polypeptide) joined at its amino- or carboxy-terminus via a peptide bond to an amino acid sequence of a different protein. In one embodiment, such a chimeric protein is produced by recombinant expression of a nucleic acid encoding the protein. The chimeric product can be made by ligating the appropriate nucleic acid sequence, encoding the desired amino acid sequences, to each other in the proper coding frame and expressing the chimeric product by methods commonly known in the art. Alternatively, the chimeric product can be made by protein synthetic techniques (e.g., by use of an automated peptide synthesizer).

Alternatively, or in addition, a eukaryotic cell expressing the wild-type protein is assayed for a biological activity associated with the wild-type protein. Eukaryotic cells expressing the wild-type protein are typically contacted with the agent in vitro or ex vivo. In certain embodiments, the eukaryotic cell expresses a heterologous nucleic acid (e.g., a recombinantly produced expression construct) encoding the wild-type protein. Methods for obtaining nucleic acids (e.g., chemical synthesis, enzymatic production, or biological production), and for their introduction into eukaryotic cells, are well-known in the art. (See, e.g., Sambrook and Russell, supra; Ausubel et al., supra; Sambrook et al., supra. See also Section II(A), supra, which describes eukaryotic expression systems for expressing neurotoxic polypeptides.)

As set forth supra in Section II(A) with respect to eukaryotic expression systems, a candidate agent can be contacted with the cell according to the characteristics of the candidate agent and the cell (e.g., contacted with a nucleic acid by transformation; or contacted with a candidate agent by culturing the cell in media containing the candidate agent (for example, by culturing the cell in liquid media, or growing the cell on solid or semi-solid media containing the candidate agent)).

Optionally, cells (e.g., congenic cells) that do not express the wild-protein are contacted with the candidate agent and assayed for the biological activity associated with the wild-type protein. In such cases, specificity of the candidate agent for the wild-type protein is generally indicated where cells that express the wild-type protein and are contacted with the agent do not show a substantial decrease in the biological activity relative to cells that do not express the wild-type protein and are contacted with the agent.

Particularly suitable biological activities that can be measured using known methods include, e.g., enzymatic activities. Enzymatic activities associated with wild-type proteins that enhance toxicity of neurotoxic polypeptides include, for example, kinase activity (e.g., HSL1, YCK2, SSK22, PKH1, YPK1, KNS1, STK29, KIAA1811, CSNK1G2, MAP3K4, MAP3K5, PDPK1, SGK2, CLK1); phosphatase activity (e.g., FIG4, SAL6, PPG1, SAC3, PPP1CB, PPP4C); GTP-binding and/or GTPase activity (e.g., SYT1, YPT53, BIG1, RAB5C, RAB5A); and protease activity (e.g., KEX1, YPS1, YPS3, YIM1, PGC), including ubiquitin-specific protease (or deubiquinating enzyme) activity (e.g., UBP2, UBP12, DOA1, BRE5, USP28, USP15).

In particular variations, enzymatic activity of protein kinases is measured using in vitro kinase assays well-known in the art. For example, isolated and purified (or partially purified) protein (e.g., recombinant or immunopurified) is incubated with a substrate in a kinase reaction buffer containing cold ATP and [α-$^{32}$P]ATP (e.g., 10 min at 30° C.). Unincorporated [γ-$^{32}$P]ATP is then separated from the substrate prior to counting. Typically, phosphorylation substrate is immobilized onto a solid matrix (for example, by spotting the reaction onto, e.g., phosphocellulose paper, or precipitating substrate from the reaction using, e.g., Sepharose beads having a label specific for the substrate (for example, glutathione-labeled beads for binding GST-tagged substrate)). The solid matrix is then washed, dried, and samples are counted.

Alternatively, cellular kinase activity is measured. For example, in certain variations, cultured eukaryotic cells expressing the wild-type protein are subjected to conditions that activate one or more signal transduction pathways mediated by the wild-type protein (e.g., pathways involved in growth, differentiation, response to stress, and/or apoptosis). Such conditions can include, for example, contacting the cells with an extracellular ligand (e.g., cytokines, growth factors, and the like) known to activate particular phosphorylation events catalyzed by the wild-type protein or subjecting the cells to particular stress activators (e.g., hypoxia, UV radiation, high osmolarity, and the like). Cells are then analyzed for phosphorylation of one or more substrates of the wild-type protein kinase. For example, in certain embodiments, cells are lysed, and cellular proteins are separated by, e.g., SDS-PAGE, transferred to a solid matrix (e.g., nitrocellulose), and immunoblotted using antibodies specific for phosphorylated substrate or particular phosphoamino acid residues. Optionally, the phosphorylation substrate is precipitated from the cellular lysate prior to SDS-PAGE (e.g., using known immunoprecipitation methods).

In other embodiments, GTP-binding and/or enzymatic activity of GTPases are measured using well-known in vitro assays. (See, e.g., Tall et al., *Mol. Biol. Cell* 10:1873-1889 (1999).) For example, in specific embodiments, GTP-binding is assessed as follows. Wild-type protein (e.g., recombinant or immunopurified protein) having GTP-binding activity is incubated in GTP binding reactions containing [γ-$^{32}$P]GTP (for example, 2 μg of protein in a 100 μl volume reaction containing 1 mM DTT, 2 mM EDTA, 0.5 mg/ml BSA, 20 mM Tris-HCl, pH 7.5, and 10 mM MgCl$_2$, with 0.25 μl of [γ-$^{32}$P]GTP (6.5×10$^4$ cpm/μl). The reactions are incubated for, e.g., 15 min at 30° C., and an aliquot is removed and added to a quenching buffer lacking [γ-$^{32}$P]GTP to stop the reaction (for example, a 10 μl aliquot is added to 1.0 ml of cold 50 mM Tris-HCl, pH 7.5, 10 mM MgCl$_2$, and 50 mM NaCl). This solution is then passed through a membrane filter (e.g., 0.45-μm nitrocellulose) and washed with quenching buffer. The filters are dried and subjected to scintillation counting. Counts that remained on the filters correspond to the amount of [γ-$^{32}$P]GTP that is associated with the wild-type protein.

In other specific variations, GTPase activity of the wild-type protein is determined as follows. Wild-type protein (e.g., 2-5 pmol of recombinant or immunopurified protein) is incubated in GTP loading reactions containing [γ-$^{32}$P]GTP (for example, 15 min at 30° C. in 50-μl reactions containing 0.025 μM [γ-$^{32}$P]GTP, 50 mM Tris-HCl, pH 8.0, 1 mM EDTA, 1 mM DTT, 0.5 μg/ml BSA, and 0.5 μM GTP). Protein-bound [γ-$^{32}$P]GTP is stabilized by the addition of, for example, buffer solution containing MgCl$_2$ (e.g., for 50 μl reactions, 2.75 μl of 100 mM MgCl$_2$ and 47.25 μl of 50 mM Tris-HCl, pH 8.0/1 mM DTT/5 mM MgCl$_2$) and kept cold (e.g., at 4° C.). The GTPase reaction is initiated by the addition of a reaction buffer at an appropriate temperature (for example, 90 μl of the stabilized loading reaction as set forth above is brought up to 450 μl in buffer 50 mM Tris-HCl, pH 8.0/1 mM DTT/5 mM MgCl$_2$, with the final concentrations of ATP and GTP adjusted to 1 mM at 30° C.). At various time points after the start of the reaction an aliquot is removed and quenched (e.g., by addition to a charcoal suspension (0.1 M HCl, 10% ethanol, and 50 mM KH$_2$PO$_4$)). Following precipitation and separation of protein from the mixture, the amount of soluble [$^{32}$P]orthophosphate is determined by liquid scintillation counting.

Other suitable biological activities that can be measured using known methods include, for example, protein-binding (e.g., CYK3, PAF1, VPS53, RNQ1, UME-1, YIR003W, RTN4IP1, STX16, BECN1, RC3, PUM2, PFDN5); vesicle-mediated transport (e.g., SH3GL2, DEF1, MSO1, VPS53, VPS60, SNA2, YBR241C, VAM3, VPS30, VPS38, VPS13, STX16, STX1B2, VPS13A); lipid metabolim (e.g., YDR287W, IMPA1, PLAA, HDLBP, SAC3, FIG4, PDR16); and salt tolerance (e.g., HAL9).

Protein-protein interactions can be assayed using any of a variety of standard in vitro or in vivo methods, including, for example, using GST-fusion proteins to co-precipitate associated proteins, coimmunoprecipitation of associated proteins, chemical cross-linking studies, yeast and bacterial two-hybrid screening systems, phage display approaches, and genetic approaches in yeast. (See generally, e.g., *Protein-Protein Interactions: A Molecular Cloning Manual* (Erica Golemis ed., Cold Spring Harbor Laboratory Press, Cold Spring Harbor, N.Y., 2002. See also, e.g., Shulewitz et al., *Mol. Cell. Biol.* 19:7123-7137 (1999); Tall et al., *Mol. Biol. Cell* 10:1873-1889 (1999).)

In yet other embodiments, cells expressing wild-type proteins regulating lipid metabolism are analyzed for the presence or absence of particular lipid species associated with the respective metabolic pathway(s). Methods for extracting lipids from cells, including, for example, triacylglycerols, phospholipids (e.g., phosphoinositides), and glycolipids, are well-known. (See generally, e.g., "Preparation of lipid extracts from tissues," In *Advances in Lipid Methodology-Two* 195-213 (W. W. Christie ed., Oily Press, Dundee, 1993.) Once extracted, lipid composition can be determined using any of various known analytical methods, including, e.g., thin layer chromatography (TLC) or high performance liquid chromatography (HPLC). In some variations, cellular lipids are metabolically labeled prior to extraction and analysis. For example, cellular phosphoinositides can be labeled by culturing cells in the presence of [$^3$H]myo-inositol.

Alternatively, the level of particular lipid species are measured in cells in situ using labeled molecules (e.g., fluorescent dyes) that preferentially bind the lipid. For example, lipid accumulation can be determined by staining cells with Nile red, a lipophilic fluorescent dye that preferentially binds neutral lipids such as, e.g., triglycerides.

2. Cells Expressing Neurotoxic Polypeptide and Wild-type Protein

The eukaryotic cell expressing the neurotoxic polypeptide and wild-type protein is contacted with the candidate agent in vitro, ex vivo, or in vivo. In certain embodiments in which the cells are contacted with the agent in vitro, the eukaryotic cells expressing the neurotoxic polypeptide and wild-type protein and, optionally, second eukaryotic cell expressing the neurotoxic polypeptide but lacking the wild-type protein are, e.g., cells of the foregoing first and second eukaryotic expression systems as described in Section II(A), supra.

Alternatively, eukaryotic cells expressing the neurotoxic polypeptide and wild-type protein, or capable of expressing the neurotoxic polypeptide and wild-type protein under certain conditions, are isolated from an animal subject (e.g., mouse or human) for use in ex vivo assays. Methods for isolation and maintenance of primary cell cultures are well-known in the art. Following isolation (and, if required, induction of expression of the neurotoxic polypeptide and wild-type protein), cells are contacted with the candidate agent as set forth above.

In yet other embodiments, the eukaryotic cell can be contacted with the candidate agent by administering the candidate agent to an animal in which the neurotoxic polypeptide is expressed (e.g., an animal model for neurodegenerative disease). For example, in certain embodiments in which the neurotoxic polypeptide is a huntingtin polypeptide comprising an expanded polyQ repeat, the candidate agent is administered to an animal model for Huntington's Disease. In other variations in which the neurotoxic polypeptide is an α-synuclein polypeptide, the candidate agent is administered to an animal model for Parkinson's Disease. Animal models for Huntington's Disease and Parkinson's Disease and which are useful in accordance with the present methods are well-known in the art. (See, e.g., Beal and Ferrante, *Nature Reviews* 5:373-384, 2004; Maries et al., *Nature Reviews* 4:727-738, 2004.) The candidate agent can be administered orally, intravenously, by infusion or injection, or the like. Candidate agents are administered to the animals either before or after onset of disease symptoms using one or more treatment regimens (based on, e.g., administration routes, dosage, frequency of dosing, and the like), and the animals are monitored for amelioration of one or more disease symptoms.

Candidate agents that are initially identified by any of the foregoing screening methods can be further tested to validate the apparent activity. Typically, such studies are conducted by re-screening the agents. Alternatively, if a candidate agent is identified in one eukaryotic cell expression system (e.g., a yeast expression system), the identified candidate agent can be further characterized in another model system, such as a rat, mouse, *Drosophila* or *C. elegans* system, or cells isolated from such an organism or ex vivo human cells. Subsequent validation also can be performed with suitable animal models. The basic format of such methods can involve administering a lead compound identified during an initial screen to an animal that serves as a model for the human neurodegenerative disease and then determining if neurotoxicity is modulated. The animal models utilized in validation studies generally are mammals of any kind. Specific examples of suitable animals include, but are not limited to, primates, mice and rats.

III. Identification of Mutations in Genes Correlated with Neurodegenerative Disease In another aspect, methods are provided to identify mutations in genes that are correlated with neurodegenerative disease. Such screening methods can be performed by analyzing the sequences of genes for which the absence of wild-type function causes toxicity or enhances toxicity of a neurotoxic polypeptide. For example, one or more such human genes can be screened to identify mutations in genes that are associated with neurodegenerative disease. For example, the sequences of one more of the following genes can be screened in samples from subjects having or at risk for developing Huntington's disease: KMO, SH3GL2, FLJ39117, TXNDC2, EDF1, MGMT, PD2, RAD54B, PPGB, FLJ10979, SS18, IMPA1, SKD, HMGB2, PERQ1, KIAA0100, SLC13A5, FLJ39117, SNRPA, NUP43, HAAO, SLC2A1, ZDHHC15, SEMG2, RANBP2, and DNAJA2. In some embodiments, the gene screened in the samples is not FLJ39117, TXNDC2, or SS18.

Similarly, the sequences of one more of the following genes can be screened in samples from subjects having or at risk for developing Parkinson's disease: FLJ10211, ADCK2, RTN4IP1, USP28, STX16, PPP1CB, BECN1, DMXL1, RC3, HDLBP, HYOU1, SGK2, USP15, VPS13A, SLC25A15, PUM2, PFDN2, HDAC6, APRT, DSPP, PFDN5, DDX6, G10, HSF4, SAC3, STK29, KIAA1811, PPP4C, CSNK1G2, MAP3K4, MAP3K5, PDPK1, CLK1, BIG1, RAB5C, RAB5A, PGC, PLAA, G3BP2, ABCC1, ABCG2, and PTPN9.

Typically, the methods comprise analyzing a nucleic acid of one or more of the above genes wild-type gene from subjects having, or at risk for developing a neurodegenerative disease. The sequence of a nucleic acid is analyzed to determine whether it contains a mutation, as compared with a nucleic acid from a wild-type nucleic acid. Such a mutation can be one or more nucleotide changes, deletions or insertions.

The sequence of the wild-type gene can be obtained from a reference library, from a healthy individual, or from a collection of individuals known not to have or to be at risk for developing the neurodegenerative disorder. The sequence of the wild-type gene also can be obtained from, for example, a sequence resulting from the Human Genome Project or a commercially available database containing such information.

Mutations in a gene can be detected by any suitable means for analyzing the sequence of a nucleic acid. For example, mutations can be detected by DNA sequence analysis, restriction fragment length polymorphism (RFLP) analysis, single-stranded length polymorphism (SSCP) analysis, allele-specific PCR, and the like. (See generally Sambrook et al., Ausubel et al., and Sambrook et al., all supra). Southern blot of genomic DNA (e.g., from a human) can be used for screening for a restriction fragment length polymorphism (RFLP) to detect the presence of a mutation associated with a neurodegenerative disorder.

In another embodiment, single nucleotide polymorphism (SNP) analysis can be used. Various real-time PCR methods including, e.g., Taqman or molecular beacon-based assays (see, e.g., U.S. Pat. Nos. 5,210,015 and 5,487,972; Tyagi et al., *Nature Biotechnology* 14:303 (1996); and PCT WO 95/13399) are useful to detect the presence or absence of a SNP. Other methods include ligase chain reaction (LCR) systems, and the nucleic acid sequence based amplification (NASBA, Cangene, Mississauga, Ontario) and Q Beta Replicase systems. These systems can be used to directly identify mutations where the PCR or LCR primers are designed to be extended or ligated only when a selected sequence is present. Alternatively, the selected sequences can be generally amplified using, for example, nonspecific PCR primers and the amplified target region later probed for a specific sequence indicative of a mutation. Various detection probes, including Taqman and molecular beacon probes can be used to monitor amplification reaction products, e.g., in real time.

Additional SNP detection methods include, for example, sequencing by nucleic acid hybridization, dot blotting, oligonucleotide array (DNA Chip) hybridization analysis, as described in, for example, e.g., U.S. Pat. No. 6,177,249; Landegren et al., *Genome Research* 8:769-76 (1998); Botstein et al., *Am. J. Human Genetics* 32:314-31 (1980); Meyers et al., *Methods in Enzymology* 155:501-27 (1987); Keen et al., *Trends in Genetics* 7:5 (1991); Myers et al., *Science* 230: 1242-46 (1985); and Kwok et al., *Genomics* 23:138-44 (1994).

In a typical embodiment, the methods comprise obtaining a biological sample, containing a nucleic acid containing a gene of interest, from a subject having or at risk for developing a neurodegenerative disease, and analyzing the nucleic acid to determine whether the gene of interest contains a mutation, as compared with a corresponding wild-type nucleic acid. The sample can be, for example, a tissue sample, blood sample, or other sample containing nucleic acids of the subject.

The nucleic acids in the sample can be either positive or negative probes. Positive probes bind to their targets and the presence of duplex formation is evidence of the presence of the target. Negative probes fail to bind to the suspect target and the absence of duplex formation is evidence of the presence of the target. For example, the use of a wild-type specific nucleic acid probe or PCR primers can serve as a negative probe in an assay sample where only the nucleotide sequence of interest is present.

IV. Methods of Analyzing Expression of Genes Enhancing Toxicity of Neurotoxic Polypeptides In a related aspect, methods of analyzing the expression of one or more genes enhancing toxicity of a neurotoxic polypeptide are provided. The detection of differences in expression of such genes has many uses. For example, as discussed herein, detection of message levels from such genes can be useful for identifying changes in gene activity associated with neurodegenerative disease or a predisposition to a neurodegenerative disease. Moreover, detection of changes in gene expression can be useful to identify modulators of gene expression and/or neurotoxic polypeptide expression.

In certain embodiments, the gene(s) analyzed for a change in expression is at least one of KMO, SH3GL2, FLJ39117, TXNDC2, EDF1, MGMT, PD2, RAD54B, PPGB, FLJ10979, SS18, IMPA1, SKD, HMGB2, PERQ1, KIAA0100, SLC13A5, FLJ39117, SNRPA, NUP43, TXNDC2, HAAO, SLC2A1, ZDHHC15, SEMG2, RANBP2, and DNAJA2. In some variations, the gene analyzed for a change in expression is not FLJ39117, TXNDC2, or SSI8. In yet other embodiments, the gene(s) is at least one of FLJ10211, ADCK2, RTN4IP1, USP28, STX16, PPP1CB, BECN1, DMXL1, HDLBP, HYOU1, SGK2, USP15, VPS13A, SLC25A15, PUM2, PFDN2, HDAC6, APRT, DSPP, PFDN5, DDX6, G10, HSF4, SAC3, STK29, KIAA1811, PPP4C, CSNK1G2, MAP3K4, MAP3K5, PDPK1, CLK1, BIG1, RAB5C, RAB5A, PGC, PLAA, G3BP2, ABCC1, ABCG2, and PTPN9.

A variety of methods for specific DNA and/or RNA measurement that use nucleic acid hybridization techniques are known to those of skill in the art (see, e.g., Sambrook and Russell, supra; Ausubel et al., supra; and Sambrook et al., supra). Some methods involve an electrophoretic separation (e.g., Southern blot for detecting DNA, and Northern blot for detecting RNA). Measurement of DNA and RNA can also be carried out in the absence of electrophoretic separation (e.g., by dot blot).

The selection of a nucleic acid hybridization format is not critical. A variety of nucleic acid hybridization formats are known to those skilled in the art. For example, common formats include sandwich assays and competition or displacement assays. Hybridization techniques are generally described in Hames and Higgins (*Nucleic Acid Hybridization, A Practical Approach*, IRL Press (1985)), Gall and Pardue (*Proc. Natl. Acad. Sci. USA* 63:378-383 (1969)), and John et al. (*Nature* 223:582-87 (1969)).

Detection of a hybridization complex may require the binding of a signal-generating complex to a duplex of target and probe polynucleotides or nucleic acids. Typically, such binding occurs through ligand and anti-ligand interactions as between a ligand-conjugated probe and an anti-ligand conjugated with a signal. The binding of the signal generation complex is also readily amenable to accelerations by exposure to ultrasonic energy.

The label can also allow indirect detection of the hybridization complex. For example, where the label is a hapten or antigen, the sample can be detected by using antibodies. In these systems, a signal is generated by attaching fluorescent or enzyme molecules to the antibodies or in some cases, by attachment to a radioactive label (see, e.g., Tjissen, "Practice and Theory of Enzyme Immunoassays," *Laboratory Techniques in Biochemistry and Molecular Biology*, Burdon and van Knippenberg Eds., Elsevier (1985), pp. 9-20).

The probes are typically labeled either directly, as with isotopes, chromophores, lumiphores, chromogens, or indirectly, such as with biotin, to which a streptavidin complex can later bind. Thus, the detectable labels used in the assays of the present invention can be primary labels (where the label comprises an element that is detected directly or that produces a directly detectable element) or secondary labels (where the detected label binds to a primary label, e.g., as is common in immunological labeling). Typically, labeled signal nucleic acids are used to detect hybridization. Complementary nucleic acids or signal nucleic acids can be labeled by any one of several methods typically used to detect the presence of hybridized polynucleotides. Typical methods of detection use autoradiography with $^{3}H$, $^{125}I$, $^{35}S$, $^{14}C$, or $^{32}P$-labeled probes or the like.

Other labels include, for example, ligands that bind to labeled antibodies, fluorophores, chemiluminescent agents, enzymes, and antibodies that can serve as specific binding pair members for a labeled ligand. An introduction to labels, labeling procedures and detection of labels is found in Polak and Van Noorden, *Introduction to Immunocytochemistry,* 2nd ed. (Springer Verlag, New York (1997)); and in Haugland, *Handbook of Fluorescent Probes and Research Chemicals*, a combined handbook and catalogue published by Molecular Probes, Inc. (1996).

In general, a detector that monitors a particular probe or probe combination is used to detect the detection reagent label. Typical detectors include spectrophotometers, phototubes and photodiodes, microscopes, scintillation counters, cameras, film and the like, as well as combinations thereof. Examples of suitable detectors are widely available from a variety of sources. Commonly, an optical image of a substrate comprising bound labeling moieties is digitized for subsequent computer analysis.

Most typically, the amount of, for example, RNA from a gene is measured by quantitating the amount of label fixed to the solid support by binding of the detection reagent. Typically, the presence of a modulator during incubation will increase or decrease the amount of label fixed to the solid support relative to a control incubation that does not comprise the modulator, or as compared to a baseline established for a particular reaction type. Means of detecting and quantitating labels are well known to those of skill in the art.

In some embodiments, the target nucleic acid or the probe is immobilized on a solid support. Solid supports suitable for use in the assays of the invention are known to those of skill in the art. As used herein, a solid support is a matrix of material in a substantially fixed arrangement.

A variety of automated solid-phase assay techniques can also be used. For instance, very large scale immobilized polymer arrays (VLSIPS™), e.g., Gene Chips or microarrays, available from Affymetrix, Inc. in Santa Clara, Calif. can be used to detect changes in expression levels of a plurality of genes involved in the same regulatory pathways simultaneously. (See Tijssen, supra.; Fodor et al., *Science* 251:767-77 (1991); Sheldon et al., *Clinical Chemistry* 39(4):718-19 (1993), and Kozal et al., *Nature Medicine* 2(7):753-59 (1996).) Similarly, spotted cDNA arrays (arrays of cDNA sequences bound to nylon, glass or another solid support) can also be used to monitor expression of a plurality of genes.

Typically, the array elements are organized in an ordered fashion so that each element is present at a specified location on the substrate. Because the array elements are at specified locations on the substrate, the hybridization patterns and intensities (which together create a unique expression profile) can be interpreted in terms of expression levels of particular genes and can be correlated with a particular disease or condition. (See, e.g., Schena et al., *Science* 270:467-70 (1995) and Lockhart et al., *Nature Biotech.* 14:1675-80 (1996).)

Hybridization specificity can be evaluated by comparing the hybridization of specificity-control polynucleotide sequences to specificity-control polynucleotide probes that are added to a sample in a known amount. The specificity-control target polynucleotides can have one or more sequence mismatches compared with the corresponding polynucleotide sequences. In this manner, whether only complementary target polynucleotides are hybridizing to the polynucleotide sequences or whether mismatched hybrid duplexes are forming is determined.

Hybridization reactions can be performed in absolute or differential hybridization formats. In the absolute hybridization format, polynucleotide probes from one sample are hybridized to the sequences in a microarray format and signals detected after hybridization complex formation correlate to polynucleotide probe levels in a sample. In the differential hybridization format, the differential expression of a set of genes in two biological samples is analyzed. For differential hybridization, polynucleotide probes from both biological samples (e.g., a control and a sample from a subject) are prepared and labeled with different labeling moieties. A mixture of the two labeled polynucleotide probes is added to a microarray. The microarray is then examined under conditions in which the emissions from the two different labels are individually detectable. Sequences in the microarray that are hybridized to substantially equal numbers of polynucleotide probes derived from both biological samples give a distinct combined fluorescence (see, e.g., PCT publication WO95/35505). In some embodiments, the labels are fluorescent labels with distinguishable emission spectra, such as, for example, Cy3 and Cy5 fluorophores.

After hybridization, the microarray is washed to remove nonhybridized nucleic acids and complex formation between the hybridizable array elements and the polynucleotide probes is detected. Methods for detecting complex formation are well known to those skilled in the art. In some embodiments, the polynucleotide probes are labeled with a fluorescent label and measurement of levels and patterns of fluorescence indicative of complex formation is accomplished by fluorescence microscopy, such as confocal fluorescence microscopy.

In a differential hybridization experiment, polynucleotide probes from two or more different biological samples are labeled with two or more different fluorescent labels with different emission wavelengths. Fluorescent signals are detected separately with different photomultipliers set to detect specific wavelengths. The relative abundances/expression levels of the polynucleotide probes in two or more samples are obtained.

Typically, microarray fluorescence intensities can be normalized to take into account variations in hybridization intensities when more than one microarray is used under similar test conditions. In some embodiments, individual polynucleotide probe/target complex hybridization intensities are normalized using the intensities derived from internal normalization controls contained on each microarray.

Detection of nucleic acids can also be accomplished, for example, by using a labeled detection moiety that binds specifically to duplex nucleic acids (e.g., an antibody that is specific for RNA-DNA duplexes). One example uses an antibody that recognizes DNA-RNA heteroduplexes in which the antibody is linked to an enzyme (typically by recombinant or covalent chemical bonding). The antibody is detected when the enzyme reacts with its substrate, producing a detectable product. Another example uses antibodies to RNA duplexes, including homo and heteroduplexes. (See, e.g., Coutlee et al., *Analytical Biochemistry* 181:153-62 (1989); Bogulavski et al., *J. Immunol. Methods* 89:123-30 (1986); Prooijen-Knegt, *Exp. Cell Res.* 141:397-407 (1982); Rudkin, *Nature* 265:472-73 (1976); Stollar, *Proc. Natl. Acad. Sci USA* 65:993-1000 (1970); Ballard, *Mol. Immunol.* 19:793-99 (1982); Pisetsky and Caster, *Mol. Immunol.* 19:645-50 (1982); Viscidi et al., *J. Clin. Microbial.* 41:199-209 (1988); and Kiney et al., *J. Clin. Microbiol.* 27:6-12 (1989).) Kits comprising antibodies specific for DNA:RNA hybrids are available, for example, from Digene Diagnostics, Inc. (Beltsville, Md.).

In addition to available antibodies, one of skill in the art can make antibodies specific for nucleic acid duplexes using existing techniques, or modify those antibodies that are commercially or publicly available. In addition to the art referenced above, general methods for producing polyclonal and monoclonal antibodies are known to those of skill in the art (see, e.g., Paul (ed), *Fundamental Immunology*, Third Edition, Raven Press, Ltd., NY (1993); Coligan, *Current Protocols in Immunology*, Wiley/Greene, New York (1991); Harlow and Lane, *Antibodies: A Laboratory Manual*, Cold Spring Harbor Press, New York (1989); Stites et al. (eds.), *Basic and Clinical Immunology*, Fourth ed., Lange Medical Publications, Los Altos, Calif., and references cited therein; Goding, *Monoclonal Antibodies: Principles and Practice,* 2d ed., Academic Press, New York, N.Y. (1986); and Kohler and Milstein, *Nature* 256:495-97 (1975)). Other suitable techniques for antibody preparation include selection of libraries of recombinant antibodies in phage or similar vectors (see, e.g., Huse et al., *Science* 246:1275-81 (1989); and Ward et al., *Nature* 341:544-46 (1989)). Specific monoclonal and polyclonal antibodies and antisera will usually bind with a $K_D$ of at least about 0.1 μM, typically at least about 0.01 μM or better, and most typically and preferably, 0.001 μM or better.

An alternative means for determining the level of expression of the nucleic acids of the present invention is in situ hybridization. In situ hybridization assays are well known. (See, e.g., Angerer et al., *Methods Enzymol.* 152:649-60 (1987).) In an in situ hybridization assay, cells, typically human cells from the brain, are fixed to a solid support, typically a glass slide. If DNA is to be probed, the cells are denatured with heat or alkali. The cells are then contacted with a hybridization solution at a moderate temperature to permit annealing of specific probes that are labeled. The probes are typically labeled with radioisotopes or fluorescent reporters.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

The following examples are offered to illustrate, but not to limit the claimed invention.

EXAMPLE 1

Screening of Yeast Deletion Set for Suppressors of PolyQ Toxicity

Yeast Gene Deletion Set Screening Methods

The yeast gene deletion set (YGDS), a collection of 4850 yeast MATa (BY4741) haploid deletion strains, was obtained frozen in glycerol stocks in 96-well microtiter dishes from Research Genetics (Huntsville, Ala.). These strains were grouped into 4 pools of approximately 1200 strains, as previously described (see Willingham et al., *Science* 302:1769, 2003). The deletion set was transformed with pYes2-Htt103Q (see Meriin et al., *J. Cell Biol.* 157:997, 2002) using the lithium acetate method (see *Guide to Yeast Genetics and Molecular Biology, Methods in Enzymology* (C. a. F. Guthrie, G. R. eds., 1991). Each pool was screened to ~12-fold coverage via selection on plates containing synthetic complete media lacking uracil (SC−Ura) for a combined total screening of ~$6.0\times10^4$ individual transformants. The total number of transformants was estimated on a control plate containing glucose as the sole carbon source (SC−Ura+glucose). Loss-of-function suppressors of Htt103Q toxicity were selected on plates containing galactose as the sole carbon source (SC−Ura+galactose). Presence of galactose induces the expression of Htt103Q via the GAL1 promoter. Plates were analyzed after 3 days of incubation at 30° C., and colonies that grew on the SC−Ura+galactose plates were selected for further analysis. Colonies underwent preliminary retesting by being streaked onto a master plate containing SC−Ura+galactose. A total of 366 transformants retained the ability to grow on plates containing galactose and were selected for further testing.

Identification of Yeast Deletion Strains that Suppress the Toxicity of Htt103Q

Colony PCR analysis was used to amplify a 20 bp barcode sequence that uniquely identifies each deletion strain for all of the 366 suppressors isolated in the screen. The PCR product was sequenced using standard DNA sequencing methods, and the barcode sequence used as a query in a blast search of the yeast gene deletion set database (http://sequence-www-.stanford.edu/group/yeast_deletion_project/deletions3.html), to identify the deletion strain. Since many of the gene deletions were isolated multiple times, the 366 suppressing strains represent a total of only 167 individual gene deletions.

Retesting of Suppressors

Fresh streaks from the original 96-well microtiter dish glycerol stocks were done for all identified suppressing deletion strains and re-transformed with pYes2-Htt103Q. Two independent transformants of each deletion strain were tested for suppression of HttQ103 toxicity using spotting assays. Spotting assays were conducted as follows. Cultures were prepared by adding 100 μl of SC−Ura+glucose media per well in 96-well microtiter plates, inoculatomg with single colonies, and incubating at 30° C. overnight. Cultures were then adjusted to a cell density of $OD_{600}$ 0.4 by dilution into SC−Ura+glucose and were incubated at 30° C. for 3 hours. Serial five-fold dilutions were made of these cultures with water, and 5 μl of each dilution was spotted onto both SC−Ura+glucose and SC−Ura+galactose plates. Glucose plates were incubated at 30° C. for 2 days, while galactose containing plates were incubated at 30° C. for 3-days. Using these spotting assays, only 27 of the 167 deletions strains identified retested for suppression of Htt103Q-mediated toxicity.

Identified Yeast Strains

Using the above methods, the following yeast deletion strains were identified as suppressors of Htt103Q-mediated toxicity: bna4Δ, cyk3Δ, def1Δ, ecm37Δ, mbf1Δ, mgt1Δ, mso1Δ, paf1Δ, rdh54Δ, rxt3Δ, sna2Δ, kex1Δ, vps53Δ, ybr016wΔ, ydr287wΔ, yer185wΔ, ylr278cΔ, ymr082cΔ, hsp104Δ, nhp6bΔ, smy2Δ, ylr454wΔ, pho87Δ, rnq1Δ, bfr1Δ, msl1Δ, ume-1Δ, yir003wΔ, ymr244c-aΔ, arg7Δ, ycl005wΔ, bna1Δ, vps60Δ, ybr241cΔ, ydr459cΔ, ymr075c-aΔ, ymr086wΔ, cox5bΔ, nup2Δ, and ydj1Δ. Of these strains, at least the following represent deletions in genes having known human orthologs: bna4Δ, cyk3Δ, def1Δ, mbf1Δ, mgt1Δ, paf1Δ, rdh54Δ, kex1Δ, vps53Δ, ybr016wΔ, ydr287wΔ, hsp104Δ, nhp6bΔ, smy2Δ, ylr454wΔ, pho87Δ, rnq1Δ, msl1Δ, ume-1Δ, yir003wΔ, bna1Δ, ybr241cΔ, ydr459cΔ, ymr086wΔ, nup2Δ, and ydj1Δ, of which at least the following correspond to known human orthologs known to be expressed in the brain: bna4Δ, cyk3Δ, mbf1Δ, mgt1Δ, ydr287wΔ, pho87Δ, bna1Δ, ybr241cΔ, and ydj1Δ.

In addition, the following strains were identified as strong suppressors: bna4Δ, cyk3Δ, def1Δ, ecm37Δ, mbf1Δ, mgt1Δ, mso1Δ, paf1Δ, rdh54Δ, rxt3Δ, sna2Δ, vps53Δ, ybr016wΔ, ydr287wΔ, yer185wΔ, ylr278cΔ, ymr082cΔ, nhp6bΔ, smy2Δ, ylr454wΔ, pho87Δ, rnq1Δ, bfr1Δ, ume-1Δ, yir003wΔ, ymr244c-aΔ, and arg7Δ. A summary of some of the known functions of the products of these genes are shown below in Table 6.

TABLE 6

Yeast strains that strongly suppress Htt103Q-mediated toxicity

| Strain | Ortholog[†] | Function |
| --- | --- | --- |
| arg7Δ | No | Ornithine metabolism; arginine biosynthesis |
| bfr1Δ | No | mRNA metabolism; defects in vacuolar targeting |
| bna4Δ | Yes | Kynurenine 3-hydroxylase |
| cyk3Δ | Yes | Cytokinesis; defective in vacuolar targeting |
| def1Δ | Yes | Involved in vacuolar import; putative prion |
| ecm37Δ | No | Possibly involved in cell wall structure |
| mbf1Δ | Yes | Transcription from Pol II promoter |
| mgt1Δ | Yes | O6-methylguanine DNA repair methyltransferase |

TABLE 6-continued

Yeast strains that strongly suppress Htt103Q-mediated toxicity

| Strain | Ortholog† | Function |
|---|---|---|
| mso1Δ | No | Component of secretory vesicle docking complex |
| nhp6bΔ | Yes | Has DNA-binding and DNA-bending activity |
| rdh54Δ | Yes | Required for mitotic diploid-specific recombination |
| paf1Δ | Yes | Transcription initiation from a Pol II promoter |
| rnq1Δ | Yes | Prion; drug resistance |
| pho87Δ | Yes | Inorganic phosphate transporter activity |
| rxt3Δ | No | Possibly involved in cell wall structure |
| sna2Δ | No | Protein-vacuolar targeting |
| smy2Δ | Yes | Unknown |
| vps53Δ | Yes | Protein sorting in late golgi |
| ume1Δ | Yes | Meiosis |
| ybr016wΔ | Yes | Putative prion |
| ydr287wΔ | Yes | Phospholipid metabolism |
| yer185wΔ | No | Response to toxin |
| yir003wΔ | Yes | Member of the F-actin capping protein complex |
| ylr278cΔ | No | Transcription from Pol II promoter; putative prion |
| ylr454wΔ | Yes | Unknown |
| ymr082cΔ | No | Unknown |
| ymr244c-aΔ | Yes | Unknown |

†The ortholog category indicates yeast genes with known mammalian orthologs.

Further, Table 7 shows some known mammalian orthologs of strong loss-of-function suppressors of Htt103Q toxicity.

TABLE 7

Mammalian orthologs of yeast loss-of-function suppressors of Htt103Q-mediated toxicity known to be expressed in the brain

| Yeast Gene | Rat Ortholog‡ | Mouse Ortholog‡ | Human Ortholog‡ |
|---|---|---|---|
| BNA4 | KMO (39%) | KMO (38%) | KMO (38%) |
| CYK3 | SH3D2A (39%) | SH3GL2 40%) | SH3GL2 (39%) |
| MBF1 | n/a | EDF1 (46%) | EDF1 (45%) |
| MGT1 | MGMT (39%) | MGMT (40%) | MGMT (41%) |
| PHO87 | SLC13A3 (22%) | SLC13A3 (22%) | SLC13A3 (22%) |
| YDR287W | IMPA1 (35%) | IMPA1 (34%) | IMPA1 (41%) |

‡Numbers in parentheses indicate % identity at the amino acid level between the yeast gene and the respective mammalian ortholog(s).

EXAMPLE 2

Screening of Yeast Deletion Set for Suppressors of α-Synuclein Toxicity

To search for loss-of-function mutations that suppress α-synuclein toxicity, a yeast homozygous diploid collection of 4768 unique open reading frames knock-outs (Open Biosystems cat # YSC1056) produced by the *Saccharomyces* Genome Deletion Project (SGDP) (see Winzeler et al., *Science* 285:901-906, 1999) was screened. Single deletion strains were pooled and transformed with a plasmid for the galactose-inducible expression of an in-frame fusion of human wild type α-synuclein and GFP proteins (p426GALSYN) (see Outerio and Lindquist, *Science* 302: 1772-1775, 2003) following the one step protocol of yeast in stationary phase (see Chen et al., *Curr. Genet.* 21:83-84, 1992). Briefly, yeast cells were grown in YPD to stationary phase and up to 11 aliquots of 0.25 ml each were made. Cells were washed with $H_2O$, resuspended in 0.1 ml of one step buffer (0.2M Lithium acetate, 40% PEG 3350, 100 mM Dithiothreitol) and transformed with 1 µg of p426GALSYN and 10 µg of salmon sperm DNA. One aliquot was transformed with 1 µg of empty p426GAL as a control of no toxicity. Transformants were selected at 30° C. in SC−ura plates containing 2% galactose and transferred to new plates after 3 days to increase the selection stringency. Transformation efficiency was estimated in plates containing 2% glucose where synuclein expression is not induced (see Outerio and Lindquist, supra).

Out of 100,000 transformants screened (aprox. 20 fold the collection size), 174 colonies that grew in galactose plates were chosen for further analysis. Genomic DNA from these strains was prepared by lysing cells in 20 mM NaOH and subsequently PCR amplified with forward (5'-GCCTCGA-CATCATCTGCCCAG-3') (SEQ ID NO:1) and reverse (5'-CGGTGTCGGTCTCGTAG-3') (SEQ ID NO:2) primers. Bar codes downstream of KANMX4 cassette were sequenced with forward primer (SEQ ID NO:1) to identify the open reading frames deleted in these particular strains (see SGDP web site for details: www-sequence.stanford.edu/group/yeast_deletion_project/deletions3.html).

Suppression of synuclein induced toxicity in these knock-out strains was further confirmed by re-transforming both the parental BY4743 and the original deletion strains from the collection with plasmids p426GAL and p426GALSYN and comparing growth in spotting assays. Cells were grown to stationary phase in liquid SC−ura plus 2% glucose and fresh cultures were started at an $OD_{600}$ of 0.4 and incubated at 30° C. for 4 hours to reach log phase. 5 fold serial dilutions were spotted in both SC−ura plus 2% glucose and SC−ura plus 2% galactose plates.

Using the above methods, the following yeast deletion strains were identified as suppressors of α-synuclein-mediated toxicity: vts1Δ, lph17Δ, yim1Δ, ubp2Δ, vam3Δ, bul1Δ, sal6Δ, yor138cΔ, vps30Δ, rav1Δ, vps38Δ, scp160Δ, kar5Δ, yjr111cΔ, yap3Δ, hal9Δ, yhl044wΔ, ykl077wΔ, lhs1Δ, ypk1Δ, ubp12Δ, vps13Δ, ycl005wΔ, yhm1Δ, puf4Δ, yer030wΔ, ybl083cΔ, gim4Δ, ycl075wΔ, mrpl13Δ, hda1Δ, ybr027cΔ, apt2Δ, pmd1Δ, gim5Δ, dhh1Δ, bud31Δ, sfl1Δ, fig4Δ, hsl1Δ, ppg1Δ, yck2Δ, ssk22Δ, spl2Δ, pkh1Δ, kns1Δ, syt1Δ, ypt53Δ, yps1Δ, yps3Δ, doa1Δ, bre5Δ, ydr119wΔ, ybt1Δ, pdr5Δ, and pdr16Δ. Of these strains, at least the following represent deletions in genes having known human orthologs: vts1Δ, lph17Δ, yim1Δ, ubp2Δ, vam3Δ, sal6Δ, vps30Δ, rav1Δ, scp160Δ, lhs1Δ, ypk1Δ, ubp12Δ, vps13Δ, yhm1Δ, puf4Δ, gim4Δ, hda1Δ, apt2Δ, pmd1Δ, gim5Δ, dhh1Δ, bud31Δ, sfl1Δ, fig4Δ, hsl1Δ, ppg1Δ, yck2Δ, ssk22Δ, pkh1Δ, kns1Δ, syt1Δ, ypt53Δ, yps1Δ, yps3Δ, doa1Δ, bre5Δ, ybt1Δ, pdr5Δ, and pdr16Δ.

In addition, the following strains were identified as strong suppressors: vts1Δ, ubp2Δ, vam3Δ, vps38Δ, scp160Δ, yap3Δ, hal9Δ, ykl077wΔ, ypk1Δ, ybl083cΔ, mrpl13Δ, apt2Δ, fig4Δ, and doa1Δ. A summary of some of the known functions of the products of these genes are shown below in Table 8.

TABLE 8

Genes corresponding to yeast deletions strains that strongly suppress α-synuclein-mediated toxicity

| Gene | Function |
|---|---|
| VTS1 | RNA-binding protein |
| UBP2 | Ubiquitin-specific protease (ubiquitin C-terminal hydrolase), cleaves at the C terminus of ubiquitin |
| VAM3 | Syntaxin homolog (t-SNARE), required for vacuolar assembly |
| VPS38 | Protein involved in vacuolar sorting |
| SCP160 | Protein involved in control of mitotic chromosome transmission, contains 14 KH domains which are found in RNA-binding proteins |

TABLE 8-continued

Genes corresponding to yeast deletions strains that strongly suppress α-synuclein-mediated toxicity

| Gene | Function |
| --- | --- |
| YAP3 | Transcription factor of the basic leucine zipper (bZIP) family |
| HAL9 | Protein involved in salt tolerance, has similarity to transcription factors |
| YKL077W | Protein of unknown function |
| YPK1 | Serine/threonine protein kinase involved in the cell integrity signaling pathway and required for endocytosis |
| YBL083C | Protein of unknown function |
| MRPL13 | Mitochondrial ribosomal protein of the large subunit |
| APT2 | Adenine phosphoribosyltransferase (APRT) |
| FIG4 | $Mg^{2+}$ dependent PI(3,5)P2 phosphoinositide 5-phosphatase involved in regulating vacuole size |
| DOA1 | Protein required in ubiquitin proteolysis and found complexed with Cdc48p |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entireties for all purposes.

What is claimed is:

1. A method of identifying an agent for decreasing cellular toxicity associated with huntingtin polypeptide, comprising:

contacting a first yeast cell with a candidate agent, wherein the first cell expresses (i) a huntingtin polypeptide comprising an expanded polyQ repeat with at least 103 consecutive glutamine residues and (ii) a wild-type BNA4 gene, wherein expression of the huntingtin polypeptide is toxic to the cell;

contacting a second yeast cell with the candidate agent, wherein the second cell expresses the huntingtin polypeptide and does not express the wild-type BNA4 gene; and determining for the first and second cells the level of cell viability relative to a cell that does not express the huntingtin polypeptide and formation of inclusion bodies in the cell, whereby if the first cell (a) exhibits a decrease of cell viability or formation of inclusion bodies relative to a control cell that has not been contacted with the candidate agent and (b) does not exhibit a decrease of cell viability or formation of inclusion bodies relative to the second cell, the agent is identified as an agent for decreasing cellular toxicity associated with huntingtin polypeptide.

2. The method of claim 1, wherein the second cell contains a null allele of the wild-type BNA4 gene.

3. The method of claim 1, wherein the second cell has a deletion of the wild-type BNA4 gene.

4. The method of claim 1, wherein the yeast cell is a *Saccharomyces cerevisiae* cell.

5. The method of claim 1, wherein the candidate agent is a small molecule, a nucleic acid, a proteinaceous agent, or a peptidomimetic.

6. The method of claim 1, wherein the candidate agent is a synthetic compound.

7. The method of claim 1, wherein the candidate agent is a natural compound.

8. The method of claim 1, wherein the contacting the cell with the candidate agent comprises transformation or culturing the cell in media containing the candidate agent.

9. The method of claim 1, wherein the huntingtin polypeptide is a fusion protein.

10. The method of claim 9, wherein the fusion protein comprises a reporter polypeptide.

11. The method of claim 9, wherein the fusion protein comprises a myc epitope.

* * * * *

UNITED STATES PATENT AND TRADEMARK OFFICE
CERTIFICATE OF CORRECTION

PATENT NO.         : 7,618,793 B2
APPLICATION NO.    : 10/970741
DATED              : November 17, 2009
INVENTOR(S)        : Paul J. Muchowski Page 1 of 1

It is certified that error appears in the above-identified patent and that said Letters Patent is hereby corrected as shown below:

At column 1, line 9, please amend the paragraph as follows:

This <u>invention</u> <s>work</s> was <s>supported in part by</s> <u>made with government support under</u> grant number <s>R01NS47237 from the</s> <u>RO1NS47237 awarded by</u> National Institutes of Health. The <s>U.S. Government may have</s> <u>government has</u> certain rights in the invention.

Signed and Sealed this
Thirteenth Day of March, 2012

David J. Kappos
*Director of the United States Patent and Trademark Office*

SEQUENCE LISTING

```
<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: PCR primer

<400> SEQUENCE: 1
gcctcgacat catctgccca g                                             21

<210> SEQ ID NO 2
<211> LENGTH: 17
<212> TYPE: DNA
<213> ORGANISM: Artificial Sequence
<220> FEATURE:
<223> OTHER INFORMATION: PCR primer

<400> SEQUENCE: 2
cggtgtcggt ctcgtag                                                  17
```